US012465673B2

(12) United States Patent
Yuds et al.

(10) Patent No.: US 12,465,673 B2
(45) Date of Patent: Nov. 11, 2025

(54) SYRINGE WARMER

(71) Applicant: Fresenius Medical Care Holdings, Inc., Waltham, MA (US)

(72) Inventors: David Yuds, Hudson, NH (US); Samiullah K. Durrani, Harvard, MA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 75 days.

(21) Appl. No.: 18/354,139

(22) Filed: Jul. 18, 2023

(65) Prior Publication Data

US 2023/0355855 A1 Nov. 9, 2023

Related U.S. Application Data

(62) Division of application No. 16/706,317, filed on Dec. 6, 2019, now Pat. No. 11,806,460.

(51) Int. Cl.
*A61M 1/36* (2006.01)
*A61M 1/16* (2006.01)
*A61M 1/34* (2006.01)

(52) U.S. Cl.
CPC ........ *A61M 1/3646* (2014.02); *A61M 1/1629* (2014.02); *A61M 1/3413* (2013.01); *A61M 1/3424* (2014.02); *A61M 1/3623* (2022.05); *A61M 2205/3331* (2013.01); *A61M 2205/3368* (2013.01); *A61M 2205/368* (2013.01)

(58) Field of Classification Search
CPC .............. A61M 1/1629; A61M 1/1664; A61M 1/3413; A61M 1/3424; A61M 1/3623; A61M 2205/368
See application file for complete search history.

(56) References Cited

U.S. PATENT DOCUMENTS 4,532,414 A * 7/1985 Shah ........................ A61M 5/44 219/535
5,092,836 A * 3/1992 Polaschegg ........... A61M 1/165 604/6.11
5,259,961 A * 11/1993 Eigendorf ........... A61M 1/3427 604/6.11
5,336,165 A 8/1994 Twardowski
5,405,333 A 4/1995 Richmond
5,431,626 A 7/1995 Bryant et al.
5,437,861 A * 8/1995 Okarma .............. A61M 1/3673 424/724
5,591,344 A * 1/1997 Kenley ................ B01D 65/022 210/764
5,643,190 A * 7/1997 Utterberg ............ A61M 1/3621 604/905

(Continued)

FOREIGN PATENT DOCUMENTS

KR 10-1420497 B1 * 7/2014 ................ A61J 9/00
WO WO-2015074999 A1 * 5/2015 ............ A61M 1/166

*Primary Examiner* — Quynh-Nhu H. Vu
(74) *Attorney, Agent, or Firm* — Fish & Richardson P.C.

(57) ABSTRACT

A method includes, after an extracorporeal blood treatment, connecting a fluid source to an access line that is connected to a patient, and delivering a fluid from the fluid source to the access line to infuse blood from the access line to the patient, wherein the fluid delivered to the access line has a temperature from about 30 degrees Celsius to about 38 degrees Celsius.

20 Claims, 11 Drawing Sheets

(56) References Cited

U.S. PATENT DOCUMENTS

| | | | | |
|---|---|---|---|---|
| 5,690,831 | A | 11/1997 | Kenley et al. | |
| 6,132,616 | A * | 10/2000 | Twardowski | A61M 1/3649 210/645 |
| 6,467,953 | B1 | 10/2002 | Faries, Jr. et al. | |
| 6,561,997 | B1 * | 5/2003 | Weitzel | A61M 1/34 604/4.01 |
| 7,226,538 | B2 * | 6/2007 | Brugger | A61M 1/3646 210/194 |
| 7,387,734 | B2 | 6/2008 | Felding | |
| 7,588,684 | B2 | 9/2009 | Brugger et al. | |
| 8,029,454 | B2 * | 10/2011 | Kelly | A61M 1/3401 604/4.01 |
| 8,122,923 | B2 * | 2/2012 | Kraus | A61J 1/2072 |
| 8,197,439 | B2 * | 6/2012 | Wang | A61M 1/15 604/67 |
| 8,273,048 | B2 | 9/2012 | Thuramalla et al. | |
| 8,394,046 | B2 | 3/2013 | Nuernberger et al. | |
| 8,512,553 | B2 * | 8/2013 | Cicchello | A61M 1/284 210/741 |
| 8,620,149 | B2 * | 12/2013 | Entenman | A61M 5/44 604/113 |
| 8,792,089 | B2 | 7/2014 | Zhang et al. | |
| 8,870,549 | B2 * | 10/2014 | Tracey | A61M 60/847 417/298 |
| 9,022,969 | B2 * | 5/2015 | Helmore | F04B 43/0054 604/533 |
| 9,265,873 | B2 | 2/2016 | Ritter | |
| 9,440,015 | B2 | 9/2016 | Ritter et al. | |
| 9,440,017 | B2 * | 9/2016 | Rohde | A61M 1/3616 |
| 9,623,164 | B2 * | 4/2017 | Meyer | A61M 1/169 |
| 10,137,257 | B2 * | 11/2018 | Landy, III | A61F 7/00 |
| 10,682,454 | B2 * | 6/2020 | Coulthard | A61M 1/3643 |
| 2004/0082904 | A1 * | 4/2004 | Houde | A61M 39/223 604/151 |
| 2011/0282197 | A1 * | 11/2011 | Martz | A61J 1/10 600/432 |
| 2020/0338255 | A1 * | 10/2020 | Hobro | A61M 1/3646 |

* cited by examiner

SYRINGE WARMER

CROSS-REFERENCE TO RELATED APPLICATIONS

This application is a divisional application of and claims the benefit of priority to U.S. application Ser. No. 16/706,317, filed on Dec. 6, 2019, the contents of which are hereby incorporated by reference.

TECHNICAL FIELD

This disclosure relates to dialysis systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

A venous access line and an arterial access line can be connected to the patient to enable the blood to be drawn from the patient and to be returned to the patient after the blood flows through the filter. At the end of the hemodialysis treatment, some residual blood that has not been returned to the patient during the treatment may remain within the access lines.

SUMMARY

In one aspect, a method includes, after an extracorporeal blood treatment, connecting a fluid source to an access line that is connected to a patient, and delivering a fluid from the fluid source to the access line to infuse blood from the access line to the patient, wherein the fluid delivered to the access line has a temperature from about 30 degrees Celsius to about 38 degrees Celsius.

Embodiments can include one or more of the following features.

In some embodiments, the fluid includes saline.

In certain embodiments, the fluid source includes a fluid receptacle.

In some embodiments, the fluid receptacle includes one or more syringes containing the fluid.

In certain embodiments, connecting the fluid source to the access line includes connecting the fluid receptacle to an end of the access line.

In some embodiments, the method further includes heating the fluid contained in the fluid receptacle.

In certain embodiments, heating the fluid contained in the fluid receptacle includes positioning the fluid receptacle proximate a heating element In some embodiments, heating the fluid contained in the fluid receptacle includes activating the heating element prior to performing extracorporeal treatment In certain embodiments, heating the fluid contained in the fluid receptacle includes positioning the fluid receptacle in a housing coupled to an extracorporeal blood treatment apparatus, wherein the housing includes the heating element.

In some embodiments, heating the fluid contained in the fluid receptacle includes positioning the fluid receptacle proximate a dialyzer of an extracorporeal blood treatment system.

In certain embodiments, heating the fluid contained in the fluid receptacle includes positioning the fluid receptacle proximate a fluid line of an extracorporeal blood treatment system.

In some embodiments, the fluid line is a dialysate line carrying dialysate fluid to a dialyzer of the extracorporeal blood treatment system.

In certain embodiments, the method further includes filling the fluid receptacle with a fluid.

In some embodiments, filling the fluid receptacle includes connecting the fluid receptacle to a fluid line of an extracorporeal blood treatment system In certain embodiments, the fluid line is a saline line coupled to a saline bag of the extracorporeal blood treatment system, and the fluid includes saline.

In some embodiments, the fluid line is a substitution line coupled to a dialysate filter of the extracorporeal blood treatment system, and the fluid includes substitution fluid.

In certain embodiments, the fluid receptacle includes a syringe, and filling the fluid receptacle includes connecting the syringe to a fluid line of an extracorporeal blood treatment system, and actuating a plunger of the syringe to draw fluid from the fluid line into the syringe.

In some embodiments, the fluid source includes a fluid line of an extracorporeal blood treatment system.

In certain embodiments, the fluid line includes a substitution fluid line of the extracorporeal blood treatment system, and the fluid includes substitution fluid.

In some embodiments, connecting the fluid source to the access line includes connecting an end of the access line to the substitution fluid line.

In a further aspect, an extracorporeal blood treatment system includes an extracorporeal blood treatment apparatus that includes a warming chamber configured to receive a fluid receptacle, and a blood component set coupled to the extracorporeal blood treatment apparatus and configured to convey fluid from a patient, through a dialyzer, and back to the patient during extracorporeal blood treatment, the blood component set including an access line, wherein the fluid receptacle is configured to be coupled to the access line to infuse blood to the patient following treatment.

Embodiments can include one or more of the following features.

In some embodiments, the fluid receptacle is coupled to a saline line of the blood component set, and the fluid receptacle is filled with saline from the saline line.

In certain embodiments, the fluid receptacle includes a syringe, and filling the fluid receptacle includes actuating a plunger of the syringe to draw saline from the saline line into the syringe.

In some embodiments, the fluid receptacle is coupled to a substitution line of the extracorporeal blood treatment apparatus, and the fluid receptacle is filled with substitution fluid from the substitution line.

In certain embodiments, the fluid receptacle includes a syringe, and filling the fluid receptacle includes actuating a plunger of the syringe to draw substitution fluid from the substitution line into the syringe.

In a further aspect, an extracorporeal blood treatment apparatus includes a housing configured to receive a fluid receptacle, and a heating element coupled to the housing and configured to heat a fluid in the fluid receptacle, wherein the fluid receptacle is configured to be coupled to an access line to infuse blood to a patient following hemodialysis treatment.

Embodiments can include one or more of the following features.

In some embodiments, the heating element is coupled to a door of the housing, and the housing is configured to position the fluid receptacle proximate the heating element when the door of the housing is in a closed position.

In certain embodiments, the heating element is positioned proximate the bottom of the housing, and the housing is configured to position the fluid receptacle above the heating element.

In some embodiments, the heating element is positioned along a wall of the housing, and the housing is configured to position the fluid receptacle proximate the heating element.

In certain embodiments, the heating element is spaced apart from the fluid receptacle when the fluid receptacle is positioned within the housing.

In some embodiments, the heating element includes an infrared heater. In certain embodiments, the heating element includes a photonic heater.

In some embodiments, the housing includes one or more mechanical attachment devices configured to position of the pair of syringes within the housing.

In another aspect, an extracorporeal blood treatment system includes an extracorporeal blood treatment apparatus, a blood component set configured to be coupled to the extracorporeal blood treatment apparatus to convey fluid from a patient, through a dialyzer, and back to the patient during extracorporeal blood treatment, the blood component set including an access line configured to be coupled to the patient, a fluid receptacle configured to be connected to the access line, and a holder configured to position the fluid receptacle adjacent a fluid line set to warm fluid in the fluid receptacle.

Embodiments can include one or more of the following features.

In some embodiments, the fluid line set includes a dialysate line configured to provide dialysate to a dialyzer of the extracorporeal blood treatment system.

In certain embodiments, the extracorporeal blood treatment system further includes an insulated door coupled to the holder and configured to cover the fluid receptacle coupled to the holder.

In some embodiments, the fluid receptacle is coupled to a saline line of the blood component set, and the fluid receptacle is filled with saline from the saline line.

In certain embodiments, the fluid receptacle includes a syringe, and filling the fluid receptacle with saline includes actuating a plunger of the syringe to draw saline from the saline line into the syringe.

In some embodiments, the fluid receptacle is coupled to a substitution line of the extracorporeal blood treatment apparatus, and the fluid receptacle is filled with substitution fluid from the substitution line.

In certain embodiments, the fluid receptacle includes a syringe, and filling the syringe with substitution fluid includes actuating a plunger of the syringe to draw substitution fluid from the substitution line into the syringe.

Advantages of the systems, devices, and methods described herein include reduced discomfort to the patient during reinfusion and flushing of the arterial access and venous access of the patient. The amount of blood that needs to be disposed of after a treatment can also be reduced. In addition, the systems, devices, and methods described herein may provide added convenience to performing dialysis treatment by providing a device for storing fluid receptacles used for flushing the arterial access and venous access of the patient during hemodialysis treatment.

Other aspects, features, and advantages will be apparent from the description and drawings, and from the claims.

DETAILED DESCRIPTION

Figure 1:
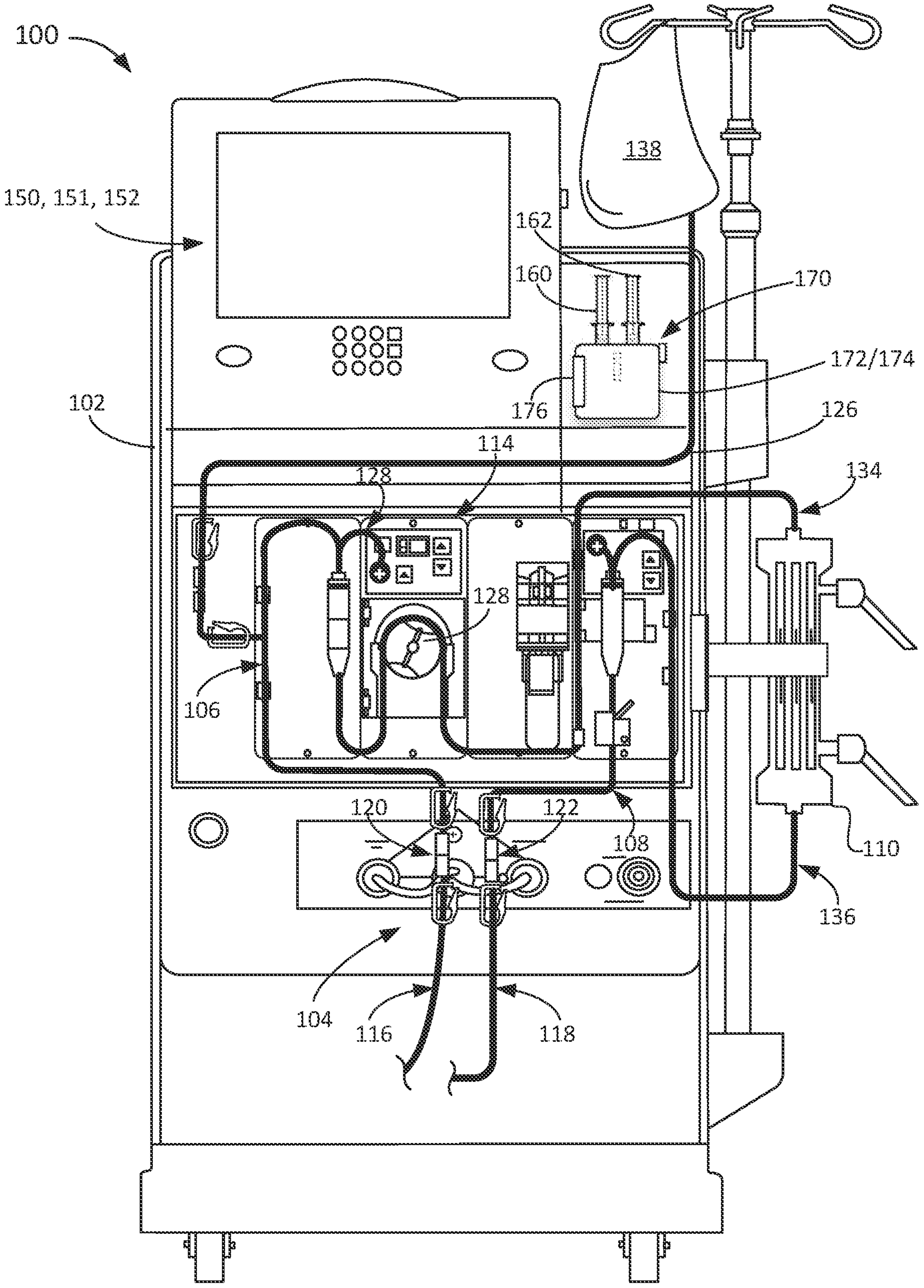
FIGS. 1 and 2 illustrate a hemodialysis system that includes a fluid warming chamber.

Referring to FIG. 1, a hemodialysis system 100 includes a hemodialysis machine 102, a disposable blood component set 104, a dialyzer 110, a blood pump 128, a saline bag 138, a saline delivery line 126, and a warming chamber 170. The disposable blood component set 104 includes an arterial line 106, a venous line 108, an arterial access line 116, and a venous access line 118. During treatment, the arterial access line 116 and venous access line 118 are coupled to the arterial line 106 and venous line 108, respectively, using connectors 120, 122. The blood pump 128 of the hemodialysis machine 102 is operable to draw blood from the patient into and through the blood component set 104 and dialyzer 110.

During hemodialysis, the arterial access line 116 and venous access line 118 are coupled at a first end to the arterial line 106 and venous line 108, respectively, and are fluidly coupled to a patient at a second end, and blood is circulated through various blood lines and components, including a dialyzer 110, of the blood component set 104. At the same time, dialysate is circulated through a dialysate circuit (shown in FIG. 4) formed by the dialyzer 110 and various other dialysate components and fluid lines connected to the hemodialysis machine 102. Many of these dialysate components and fluid lines are located inside the housing of the hemodialysis machine 102, and are thus not visible in FIG. 1. The dialysate passes through the dialyzer 110 along with the blood. The blood and dialysate passing through the dialyzer 110 are separated from one another by a semi-permeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

Still referring to FIG. 1, the dialysate circuit of the hemodialysis machine 102 is formed by multiple dialysate components and fluid lines positioned inside the housing of the hemodialysis machine 102 as well as the dialyzer 110, a dialyzer inlet line 134, and a dialyzer outlet line 136 that are positioned outside of the housing of the hemodialysis machine 102. The dialyzer inlet line 134 includes a connector adapted to connect to one end region of the dialyzer 110, and the dialyzer outlet line 136 includes a connector adapted to connect to another end region of the dialyzer 110.

Still referring to FIG. 1, the hemodialysis machine 102 includes a user interface system 150 that is operable to monitor and to control operations of the machine 102. The user interface system 150 includes a touchscreen 151 and a display 152. An operator can manually operate the touchscreen 151 to control operations of the machine 102, and the display 152 can provide visual indications to the operator. The user interface system 150 is integral to the machine 102.

The blood component set 104 of the hemodialysis system is secured to a module 114 attached to the front of the hemodialysis machine 102. The module 114 includes a blood pump 128 capable of driving blood through the blood circuit. The module 114 also includes various other instruments capable of monitoring the blood flowing through the blood circuit. The module 114 includes a door that when closed cooperates with the front face of the module 114 to form a compartment sized and shaped to receive the blood component set 104. In the closed position, the door presses certain blood components of the blood component set 104 against corresponding instruments exposed on the front face of the module 114. This arrangement facilitates control of the flow of blood through the blood circuit and monitoring of the blood flowing through the blood circuit.

After the end of the extracorporeal treatment, blood component set 104 and the dialyzer 110 may contain residual blood drawn from the patient during the hemodialysis treatment. This blood can be returned to the patient to reduce patient blood loss using the blood reinfusion process described herein. However, even after performing a reinfusion process, the arterial access line 116 and the venous access line 118 may still contain blood drawn from the patient during the hemodialysis treatment. The remaining blood in the arterial access line 116 and the venous access line 118 may be flushed to prevent clotting at the patient's access sites.

A pair of saline-filled syringes 160, 162 is provided to flush any remaining blood in the access lines 116, 118 back to the patient following dialysis treatment and reinfusion. For example, as described in further detail herein, following treatment and reinfusion, the access lines 116, 118 can be disconnected from the arterial and venous lines 106, 108, and a first syringe 160 can be coupled to the arterial access line 116 and a second syringe 162 can be coupled to the venous access line 118. The saline contained in the syringes 160, 162 can be injected into the access lines 116, 118 to flush any remaining blood in the access lines 116, 118 back to the patient.

As described in further detail herein, the saline contained in the syringe 116, 118 can be heated in the warming chamber 170 of the hemodialysis machine 102 prior to injection of the saline into the access lines 116, 118. Heating the saline contained in the syringes 160, 162 prior to flushing the access lines 116, 118 with the saline in the syringes 160, 162 can reduce the discomfort experienced by the patient during reinfusion.

As depicted in FIG. 1, the warming chamber 170 includes a housing 172 coupled to the hemodialysis machine 102. The housing 172 is configured to hold the two saline-filled syringes 160, 162. The housing 172 includes an insulating material, such as plastic, fiberglass, aerogel, cellulose, or polyurethane, to retain heat within the warming chamber 170. For example, the interior surfaces of the housing 172 can include the insulating material. The housing can be made of any of a variety of suitable materials, such as metal or plastic materials.

The housing 172 includes a door 174 that can be opened to provide access to the syringes 160, 162 positioned in the warming chamber 170 and closed the retain heat within the warming chamber 170. The door 174 is coupled to the housing 172 with a hinge 176. The door 174 includes an insulating material, such plastic, fiberglass, aerogel, cellulose, polyurethane, or fabric with infrared reflecting surface (e.g., aluminum foil). For example, the interior surface of the door 174 can include the insulating material to help retain heat within the warming chamber when the door 174 of the housing 172 is in a closed position (as depicted in FIG. 1).

Figure 2:
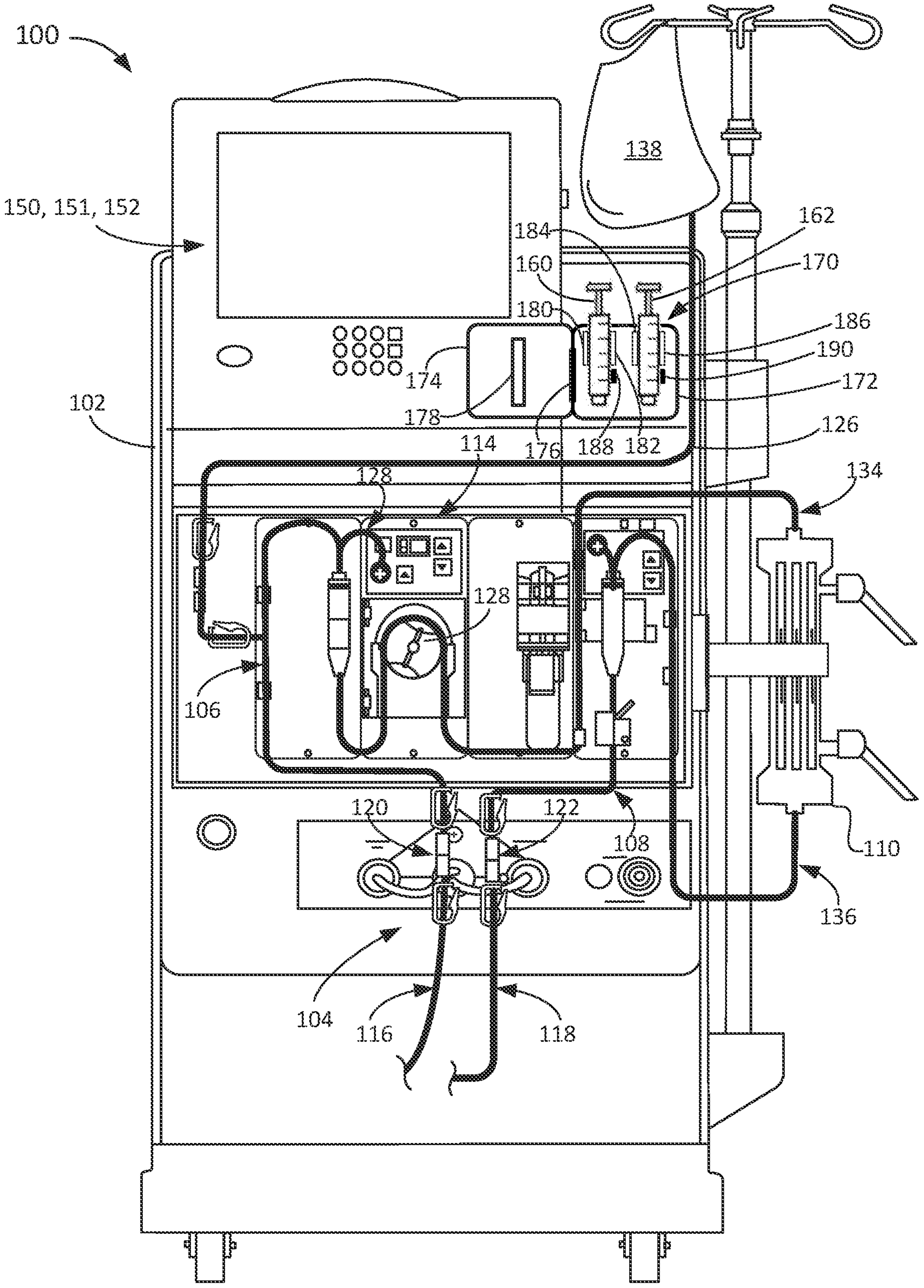

FIG. 2 depicts the hemodialysis machine 102 of FIG. 1 with the door 174 of the warming chamber 170 in an open position. As depicted in FIG. 2, the interior of the housing 172 of the warming chamber 170 includes clips 180, 182, 184, 186. The clips 180, 182, 184, 186 are configured to couple the syringes 160, 162 to the warming chamber 170 and maintain the position of the syringes 160, 162 within the warming chamber 170. For example, the syringes 160, 162 can be positioned in the warming chamber 170 during hemodialysis treatment by attaching the syringes 160, 162 to the clips 180, 182, 184, 186 and closing the door 174 of the warming chamber 170.

As depicted in FIG. 2, the warming chamber 170 also includes a heating element 178 coupled to the interior of the door 174 of the warming chamber 170. The heating element 178 is coupled to the door 174 such that the heating element 178 is positioned between each of the syringes 160, 162 when the syringes 160, 162 are coupled to the clips 180, 182, 184, 186 of the warming chamber 170. Further, the heating element 178 is positioned such that when the syringes 160, 162 are coupled to the warming chamber with the clips 180, 182, 184, 186 and the door 174 of the warming chamber 170 is closed, the heating element 178 is positioned close to each of the syringes 160, 162 without touching the syringes 160, 162. The heating element 178 provides radiated heat to the warming chamber 170. As described in further detail herein, the heating element 178 can be turned on to heat the saline contained in the syringes 160, 162 in the warming chamber 170. Any of various suitable photic or infrared heating elements can be used, such as metal resistance wire, ceramic, semiconducting materials, or a point-wise self-regulating polymer PTC resistive heater. The heating element 178 is configured to provide radiated heat to the warming chamber 170 in order to heat the interior of the warming chamber 170 to a temperature ranging from about 30 degrees Celsius to about 38 degrees Celsius.

Still referring to FIG. 2, the warming chamber 170 also includes temperature sensors 188, 190 positioned on an interior wall of the housing 172 of the warming chamber 170. The temperature sensors 188, 190 are configured to measure the temperature of the interior of the warming chamber 170. For example, as depicted in FIG. 2, the temperature sensors 188, 190 are positioned on the interior wall of the housing 172 such that when the syringe 160, 162 are positioned in the warming chamber 170 with clips 180, 182, 184, 186, the temperature sensors 188, 190 are proximate the syringes 160, 162 and measure the temperature of the warming chamber 170 near the syringes 160, 162. The temperature sensors 188, 190 can be electronically coupled to a computing device to monitor and display the temperature inside the warming chamber 170.

Figure 3:
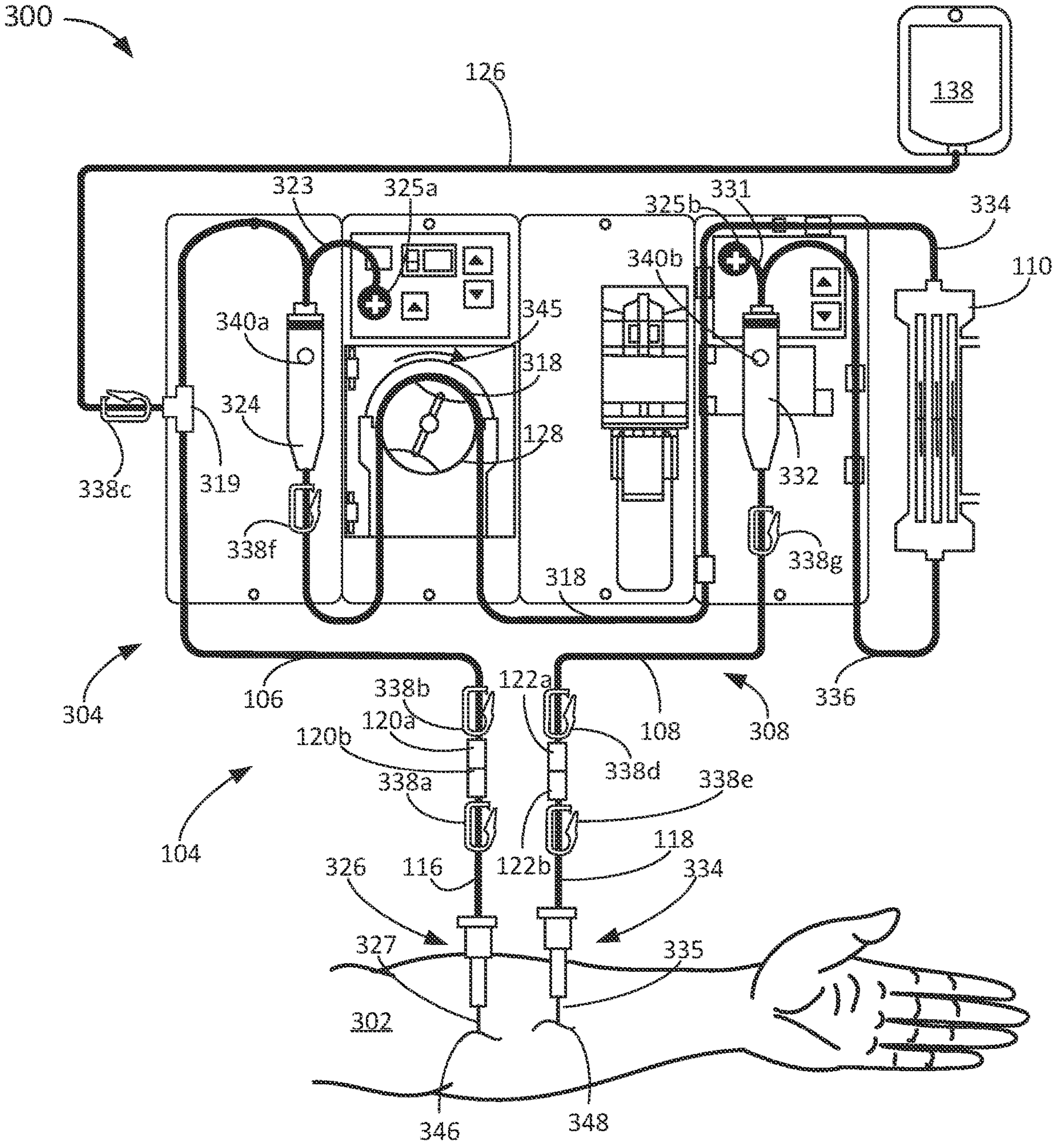
FIG. 3 is a schematic of a blood circuit of the hemodialysis system of FIG. 1.

Based on the temperature of the warming chamber 170 measured by the temperature sensors 188, 190, the temperature of the saline contained in the syringes 160, 162 in the warming chamber 170 can be determined. For example, an algorithm correlating the temperature of the interior of the warming chamber 170 with the temperature of the saline in syringes 160, 162 positioned within the warming chamber 170 can be used to determine the temperature of the saline in the syringes 160, 162. By using the readings from the temperature sensors 188, 190 to determine and monitor the temperature of the saline in the syringes 160, 162, a user can determine when the temperature of the saline in the syringes 160, 162 is in a range of about 30 degrees Celsius to about 38 degrees Celsius (e.g., 36.5 degrees Celsius to 37.5 degrees Celsius), which provides improved comfort when injecting the saline to flush the access lines 116, 118. Any of various suitable temperature sensors can be used, such as bi-metallic thermostat, thermistors, thermocouples, semi-conductor sensors, or infrared sensors. FIG. 3 is a schematic showing the flow paths of fluids into, through, and out of the blood circuit 300 of the hemodialysis system 100. As depicted in FIG. 3, the blood component set 104 includes an arterial line set 304 and a venous line set 308.

The arterial line set 304 includes the arterial access line 116, the arterial line 106, and an arterial drip chamber 324. The arterial line 106 extends at a first end from the arterial access line 116 to a port 319, which connects the arterial line 106 to the saline line 126. The arterial line 106 is connected at a second end to the arterial drip chamber 324. A pressure transducer 325*a* is connected to the arterial drip chamber 324 via a pigtail line 323 extending from the arterial drip chamber 324 and is configured to detect a fluid pressure within the arterial drip chamber 324. A U-shaped pump line 318 extends from the bottom of the arterial drip chamber 324 and is connected to a dialyzer inlet line 334. The dialyzer inlet line 134 is connected via a tube adaptor to a blood entry port of the dialyzer 110.

A manually operable connector 120*a* at the end of the arterial line 106 is configured to connect to a manually operable connector 120*b* at the end of the arterial access line 116. During hemodialysis treatment, the arterial line 106 is connected to the arterial access line 116, and the arterial access line 116 is connected to an arterial needle assembly 326. The arterial needle assembly 326 includes a needle 327 that is insertable into the arterial access 346 of the patient 302. During hemodialysis treatment, the arterial needle assembly 326 is connected to the arterial access line 116 and the needle 327 of the arterial needle assembly 326 is inserted into the patient 302 to enable blood to be drawn from the patient 302 into the arterial line set 304. For example, the blood pump 128 pumps blood from the artery of the patient 302 through the arterial needle assembly 326, the arterial access line 116, and the arterial line 106 to the dialyzer 110.

The venous line set 308 includes the venous access line 118, the venous line 108, and a venous drip chamber 332. A dialyzer outlet line 336 extends from the dialyzer 110 to the venous drip chamber 332. A pressure transducer 325*b* is connected to the venous drip chamber 332 via a pigtail line 331 extending from the venous drip chamber 332 and is configured to detect a fluid pressure within the venous drip chamber 332.

One end of the venous line 108 is connected to a bottom of the venous drip chamber 332, and the other end of the venous access line 118 is connected to the venous access line 118. A manually operable connector 122*b* at the end of the venous access line 118 is configured to connect to a manually operable connector 122*a* at the end of the venous line 108. During hemodialysis treatment, the venous line 108 is connected to the venous access line 118, and the venous access line 118 is connected to the venous needle assembly 334. The venous needle assembly 334 includes a needle 335 that is insertable into the patient 302 to enable filtered blood, e.g., blood that has travelled through the dialyzer 110, to be returned to the patient 302 through the venous line 108 and venous access line 118.

The arterial line set 304 and the venous line set 308 form an extracorporeal blood circuit through which the blood of the patient 302 circulates. The blood pump 128, when operated during the extracorporeal treatment, causes blood to flow from the patient 302, through the extracorporeal blood circuit 300 and the dialyzer 110, and then back into the patient 302 after filtration has occurred in the dialyzer 110.

The blood circuit 300 further includes one or more flow regulators engageable with the arterial line set 304, the venous line set 308, and the saline line 126. The flow regulators can be manually operable, electronically addressable, or both. In the embodiment illustrated in FIG. 3, for example, the blood circuit 300 includes a set of manually operable clamps 338*a*-338*e*. Clamp 338*a* is positioned to engage the arterial access line 116. Clamp 338*b* is positioned to engage the arterial line 106. Clamp 338*c* is positioned to engage the saline line 126. Clamp 338*d* is positioned to engage the venous line 108. Clamp 338*e* is positioned to engage the venous access line 118. The clamps 338*a*-338*e* can be independently actuated to control fluid flow through the arterial line set 304, the venous line set 308, and the saline line 126.

The blood circuit 300 also includes a set of automatic clamps 338*f* and 338*g*, which function to clamp the lines extending from the arterial drip chamber 324 and the venous drip chamber 332, respectively. As described in further detail herein, a controller of the hemodialysis machine is used to control the position of clamps 338*f* and 338*g* to allow for filling of the drip chambers 324, 332.

In some implementations, the blood circuit 300 includes one or more fluid flow sensors. In the embodiment shown in FIG. 3, a fluid flow sensor 340*a* is positioned to detect fluid flow through the arterial drip chamber 324, and a fluid flow sensor 340*b* is positioned to detect fluid flow through the venous drip chamber 332. The fluid flow sensors 340*a*, 340*b* can be optical sensors responsive to drops of fluid through the arterial drip chamber 324 and the venous drip chamber 332, respectively. The fluid flow sensors 340*a*, 340*b* can detect flow rates of fluid flowing through the arterial drip chamber 324 and the venous drip chamber 332, respectively. In addition, the fluid flow sensors 340*a*, 340*b* can distinguish between fluids having different opacities, such as blood and saline. For example, during operation of the blood pump 128, the type of fluid flowing through the arterial drip chamber 324 and the venous drip chamber 332 may vary depending on the stage of the hemodialysis treatment or the blood reinfusion process. The fluid flow sensors 340*a*, 340*b* can distinguish between the different types of fluid and provide a signal indicative of a current stage of the extracorporeal treatment or the blood reinfusion process.

In addition to the blood lines forming the main blood circuit 300, a saline delivery line 126 can be connected to the blood circuit 300 for the introduction of saline into the blood circuit 300 (e.g., during priming and reinfusion). As depicted in FIG. 3, the saline delivery line 126 is connected at a first end to a saline bag 338 and at a second end to the port 319. The port 319 fluidly couples the saline delivery line 126 to the arterial line 106 upstream of the arterial drip chamber 324.

The various blood lines, access lines, and the saline delivery line 126 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

The various blood lines and the saline delivery line 126 are typically retained within the module 114 (as depicted in FIG. 1). Various techniques can be used to secure the lines to the module 114. For example, a carrier body with a series of apertures and recesses for capturing and retaining the various blood lines and components can be secured to the module 114 of the hemodialysis machine 102. In some examples, mechanical attachment devices (e.g., clips or clamps) can be attached to a carrier body and used to retain the lines, and the carrier body can be attached to the module 114 of the hemodialysis machine 102. As another example, the lines can be adhered to or thermally bonded to a carrier body, and the carrier body can be attached to the module 114 of the hemodialysis machine.

Figure 4:
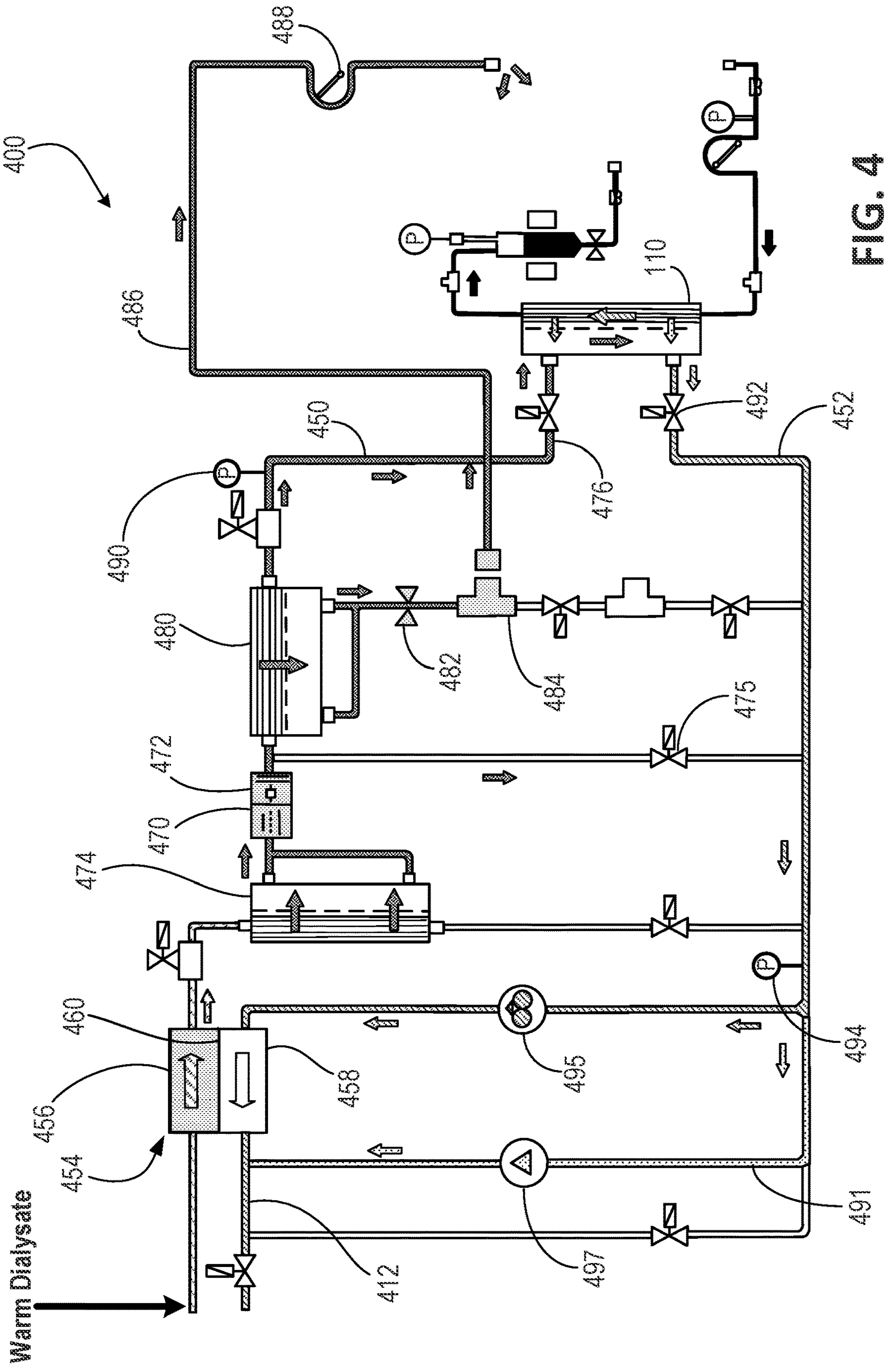
FIG. 4 is a schematic of a dialysate circuit of the hemodialysis system of FIG. 1.

FIG. 4 is a schematic showing the flow paths of fluids into, through, and out of the dialysate circuit 400. The dialysate circuit 400 includes a number of dialysate components that are fluidly connected to one another via a series of fluid lines.

Still referring to FIG. 4, the flow pump 495 of the dialysate circuit 400 is configured to draw water into the dialysate circuit 400 from a water inlet port (not shown). The water drawn into the dialysate circuit 400 by the flow pump 495 is provided to a heat exchanger of the dialysate circuit 400 (not shown) in order to warm the water received by the dialysate circuit 400. After exiting the heat exchanger, the warmed water flows to a deaeration and heating chamber (not shown) configured to heat and deaerate water received by the dialysate circuit 400.

The warmed and deaerated water flows to a mixing chamber (not shown) where the water is mixed with acid concentrate and bicarbonate concentrate to form warmed dialysate. In some examples the dialysate circuit 400 includes an acid concentrate pump coupled to a source of acid concentrate and a bicarbonate pump coupled to a source of bicarbonate to provide acid concentrate and bicarbonate concentrate, respectively, to the mixing chamber of the dialysate circuit 400 to mix with water and form dialysate.

The warm dialysate is drawn into a balancing device 454 connected to a fluid line downstream of the mixing chambers. The balancing device 454 is divided by a flexible membrane 460 into a first chamber half 456 and a second chamber half 458. As fluid flows into the first chamber half 456, fluid is forced out of the second chamber half 458, and vice versa. For example, as fresh dialysate flows into first chamber half 456 of the balancing device 454, spent dialysate is forced to flow out of the second chamber half 458 of the balancing device 454 towards the drain. In contrast, as spent dialysate flows into the second chamber half 458 of the balancing device 454, fresh dialysate is forced out of first chamber half 456 of the balancing device 454 towards the dialyzer 110. This balancing device construction and alternating flow of fresh and spent dialysate helps ensure that the volume of fresh dialysate entering the dialysate circuit is equal to the volume of spent dialysate exiting the dialysate circuit, when desired, during treatment.

During hemodialysis, fresh dialysate passing through the first chamber half 456 of the balancing device 454 is directed to the dialyzer 110 through a dialysate filter 474. The fresh dialysate flowing out of balancing device 454 flows along a fluid line through the dialysate filter 474, which is configured to filter the fresh dialysate received from the balancing device 454. One example of such a dialysate filter 474 is the DIASAFE®plus dialysis fluid filter available from Fresenius Medical Care. During hemodialysis, a bypass valve 475 is closed in order to direct the flow of dialysate from the dialysis filter 474 towards dialyzer 110.

After filtration by dialysate filter 474, the fresh dialysate flows through a conductivity cell 470 and a temperature monitor thermistor 472 downstream of the of the dialysate filter 474. The conductivity cell 470 and temperature monitor thermistor 472 regulate the temperature of the filtered dialysate exiting the dialysate filter 474. After flowing through the conductivity cell 470 and temperature monitor thermistor 472, the filtered dialysate flows through a second filter 480. The second filter 480 further filters the dialysate to generate substitution fluid.

When a dialyzer inlet valve 476 is in a closed position and a substitution valve 482 is in an open position, the substitution fluid exits the second filter 480 and flows through a substitution port 484 and along a substitution fluid line 486. As depicted in FIG. 4, a substitution pump 488 is provided along the substitution fluid line 486 to draw the substitution fluid through the substitution port 484 to the substitution line 486.

In contrast, when the dialyzer inlet valve 476 is in an open position and the substitution valve 482 is in a closed position, the substitution fluid exits the second filter 480 and flows along a dialysate inlet line 450 towards the dialyzer 110. Before entering the dialyzer 110, the substitution fluid flows through a pressure sensor 490 positioned along the dialysate inlet line 450. The pressure sensor 490 is configured to measure the pressure of the fluid entering the dialyzer 110. Any of various different types of pressure sensors capable of measuring the pressure of the substitution fluid entering the dialyzer 110 can be used, such as ultrasonic sensors, piezoresistive strain gauges, capacitive sensors, electromagnetic sensors, or piezoelectric sensors.

After flowing through the dialyzer 110, spent substitution fluid exits the dialyzer 110 through the dialyzer outlet valve 492 along a dialysate outlet line 452 of the dialysate circuit 400. A pressure sensor 494 located along the dialysate outlet line 452 is adapted to measure the pressure of the spent substitution fluid exiting the dialyzer 110. Any of various different types of pressure sensors capable of measuring the pressure of the spent substitution fluid passing from the dialyzer 110 can be used, such as ultrasonic sensors, piezoresistive strain gauges, capacitive sensors, electromagnetic sensors, or piezoelectric sensors.

A dialysate flow pump 495 is configured to pump the spent substitution fluid from the dialyzer 110 to the second chamber half 458 of the balancing device 454. As the second chamber half 458 of the balancing device 454 fills with the spent substitution fluid, fresh dialysate within the first chamber half 456 of the balancing device 454 is expelled towards the dialyzer 110. Subsequently, as the first chamber half 456 of the balancing device 454 is refilled with fresh dialysate, the spent substitution fluid is forced out the second chamber half 458 of the balancing device 454 along the drain line 412 to the drain.

As shown in FIG. 4, an ultrafiltration line 491 is connected the drain line 412 and fluidly coupled to the dialyzer 110. An ultrafiltration pump 497 is operatively connected to the ultrafiltration line 491 such that when the ultrafiltration pump 497 is operated, spent substitution fluid can be directed to the drain via the ultrafiltration line 491. Operation of the ultrafiltration pump 497 while simultaneously operating the dialysate flow pump 495 causes increased vacuum pressure within the dialysate outlet line 452 and ultrafiltration line 491, and thus creates increased vacuum pressure within the dialyzer 110. As a result of the increased vacuum pressure, additional fluid is pulled from the blood circuit 300 into the dialysate circuit 400 across the semi-permeable structure (e.g., semi-permeable membrane or semi-permeable microtubes) of the dialyzer 110. Thus, the ultrafiltration pump 497 can be operated to remove excess fluid from the patient.

The various fluid lines and drain line 112 of the dialysate circuit 400 can be formed of any of various different medical grade materials. Examples of such materials include PVC, polyethylene, polypropylene, silicone, polyurethane, high density polyethylene, nylon, ABS, acrylic, isoplast, polyisoprene, and polycarbonate.

An example process of hemodialysis treatment and blood reinfusion are described with respect to FIGS. 2-5.

Before the hemodialysis treatment is initiated, a human operator, e.g., a patient, a clinician, a nurse, or other clinical personnel, positions the arterial line set 304, the venous line set 308, the saline line 126, and the saline bag 338 in preparation for the hemodialysis treatment. The operator also mounts the arterial drip chamber 324 and the venous drip chamber 332 adjacent the fluid flow sensors 340*a*, 340*b* to enable the fluid flow sensors 340*a*, 340*b* to detect fluid flow through the arterial drip chamber 324 and the venous drip chamber 332, respectively. The operator mounts the dialyzer 110 to the hemodialysis machine 102 and connects the blood component set 104 to the dialyzer 110. The operator also connects the saline line 126 to the port 319 coupled to the arterial line 106 to place the saline bag 138 in fluid communication with the blood circuit 300.

Before performing the hemodialysis treatment, the operator primes the blood circuit 300. Referring to FIGS. 3 and 4, a method of priming the blood circuit 300 for hemodialysis treatment will now be described. During priming, clamp 338*c* to allow saline flow through the saline line 126 into the blood circuit 300. Clamp 338*b* is in a closed position to prevent fluid from flowing out the patient end of the arterial line 106. Clamp 338*d* is in an open position to allow fluid to flow out the patient end of the venous line 108 and the patient end of the venous line 108 is attached to a drain bucket (not shown). During the priming process, the arterial line 106 and the venous line 108 are not connected to the patient (as depicted in FIG. 3). Rather, during the priming process, a first end of the arterial line 106 and a first end of the venous line 108 are coupled to the blood circuit 300, and a second end the arterial line 106 and a second end of the venous line 108 are coupled to a drain or a drain bucket (not pictured).

To begin priming the system 300, saline is introduced from the saline bag 138 into the blood circuit 300 via the arterial line 106. To draw the saline from the saline bag 138 through the arterial line 106 and into the blood circuit 300, the blood pump 128 is turned on. The blood pump 128 draws the saline from the saline bag 138, through saline line 126 and the arterial line 106, through the pressure transducer 325*a*, through fluid flow sensor 340*a*, into and fills the arterial drip chamber 324. Once the arterial drip chamber 324 is filled (as detected by pressure transducer 325*a*), clamp 338*f* is automatically opened and the blood pump 128 draws saline through the pump line 318 towards the dialyzer 110. The saline flows into the dialyzer 110 via the dialyzer inlet line 334 and exits the dialyzer 110 via the dialyzer outlet line 336.

As the saline flows through the dialyzer outlet line 336 towards the venous drip chamber 332, the saline passes through the pressure transducer 325*b* and fluid flow sensor 340*b*. The saline flows into and fills the venous drip chamber 332. Once the venous drip chamber 332 is filled with saline (as detected by pressure transducer 325*b*), clamp 338*g* is automatically opened and saline flows through the venous line 108 towards the patient end of the venous line 108. Once the entire blood circuit 300 is filled with saline, any additional (e.g., excess) saline pumped through the blood component set 104 exits the patient end of the venous line 108 and is captured by a drain bucket. Once all air is out of the arterial and venous lines 106, 108 and the blood circuit 300 is filled with saline, clamps 338*c* and 338*d* are closed, and the arterial line 106 and the venous line 108 are connected together via a sterile recirculation connector, and the saline contained within the blood circuit 300 is recirculated through the blood circuit 300 until the patient 302 is ready for treatment.

Before performing the hemodialysis treatment, the operator opens the door 174 of the warming chamber 170 and couples the saline-filled syringes 160, 162 to the warming chamber 170 by attaching the syringes 160, 162 to the clips 180, 182, 184, 186 of the warming chamber 170, as depicted in FIG. 2. Once the syringes 160, 162 are positioned in the warming chamber 170 using the clips 180, 182, 184, 186, the operator closes the door 174 of the warming chamber 170 (as depicted in FIG. 1). The heating element 178 is automatically turned on once the door 174 of the warming chamber 170 is in the closed position (as depicted in FIG. 1). For example, the machine 102 can include a switch that is triggered when closing the door to activate the heating element 178. Once the heating element 178 has been turned on, the heating element begins to warm the interior of the warming chamber 170, which warms the saline contained in the syringes 160, 162.

The operator then connects the arterial access line 116 to the arterial needle assembly 326 and connects the venous access line 118 to the venous needle assembly 334. Once the access lines 116, 118 are connected to the needle assemblies 326, 334, the operator inserts the arterial needle 327 into an arterial access 346 of the patient 302, and inserts the venous needle 335 into a venous access 348 of the patient 302. The operator then removes any air contained in the access lines 116, 118. In some implementations, air contained in the access lines is removed by connecting an empty syringe (not shown) to the end of each of the access lines 116, 118 opposite the needle assemblies 326, 334, and actuating the plunger of each empty syringe to draw blood into the access lines 116, 118 to displace any air contained in the access lines 116, 118. In some implementations, the blood pressure of the patient 302 is used to draw blood into the access lines 116, 118 to displace any air contained in the access lines 116, 118. In some implementations, the access lines 116 are filled with saline using a syringe prior to inserting the needle assemblies 326, 334 into the patient 302 in order to remove air from the access lines 116, 118. Once the access lines 116, 118 are filled with fluid (e.g., blood or saline), the access lines 116, 118 are clamped using clamps 338*a* and 338*e*, respectively.

Once the blood circuit 300 has been primed and the access lines 116, 118 have been fluidly coupled to the patient and clamped, the arterial access line 116 is coupled to the arterial line 106 via connectors 120*a*, 120*b*, and the venous access line 118 is coupled to the venous line 108 via connectors 122*a*, 122*b*. Connectors 120*a*, 120*b*, 122*a*, and 122*b* can include any suitable type of connector, such as luer-lock connectors. Once the access lines 116, 118 have been attached to the arterial line 106 and venous line 108, hemodialysis is initiated.

Referring to FIGS. 3 and 4, a method of performing dialysis treatment using the hemodialysis system 100 will now be described. The operator initiates the hemodialysis treatment using a control on touchscreen 151. During the hemodialysis treatment, the blood pump 128 is operated to circulate blood through the dialyzer 110. A controller of the hemodialysis machine 102 can be used to control the blood pump 128 through feedback control based on pressures detected by the pressure transducers 325, 325*b* or based on flow rates detected by the fluid flow sensors 340*a*, 340*b*. The blood pump 128 is driven such that blood in the arterial line set 104 is drawn from the patient 302 and directed toward the dialyzer 110, and through the venous line set 108 back into the patient 302.

Referring to FIG. 4, the dialysis flow pump 495 is operated to circulate dialysis fluid through the dialyzer 110 during hemodialysis treatment. Waste substances from the blood diffuse into the dialysis fluid. In addition, in some implementations, the ultrafiltration pump 497 is operated to draw excess fluid from the extracorporeal blood circuit 300 into the dialysate circuit 400 and to the drain.

After the end of the extracorporeal treatment, an operation to deactivate the blood pump 128, the dialysis fluid pump 495, and the ultrafiltration pump 497 is initiated. For example, a controller of the hemodialysis machine 102 can automatically stop the extracorporeal treatment after predetermined criteria are fulfilled, e.g., a certain amount of time has elapsed or a certain amount of ultrafiltrate has been removed from the blood.

After the operation of the pumps 128, 495, 497 has been stopped, blood drawn from the patient 302 during the hemodialysis treatment may be present in the arterial line set 304 and the venous line set 308. A blood reinfusion process is used to return the blood contained in the arterial line 106 and the venous line 108 is to the patient 302 through the venous access 348 of the patient 302. Before the blood reinfusion process is initiated, each of the clamps 138*a* and 338*b* is closed to inhibit flow through the arterial needle assembly 326, and the arterial access line 116 is disconnected from the arterial line 106. Clamp 338*c* is opened to fluidly connect the arterial line 106 to the saline line 126 and allow saline to flow from the saline bag 138 into and through the blood circuit 300.

Once the saline line 126 is fluidly connected to the blood circuit 300, the blood pump 128 is operated to draw the saline from the saline bag 138 and circulate the saline throughout all components of the blood circuit 300 to push any blood remaining in the blood circuit 300 back to the patient 302 and fill the blood circuit 300 with saline. The blood contained in the blood circuit 300 is returned to the patient 302 through the venous needle assembly 334 and enters the patient 302 through the venous access 348. Once the majority of the blood contained in the blood circuit 300 has been reinfused back to the patient 302, clamps 338*d* and 338*e* are closed to clamp the venous line 108 and venous access line 118, respectively. Once clamped, the venous access line 118 is disconnected from the venous line 108.

While the reinfusion process described above flushes the majority of the blood contained within the venous access line 118 and the venous needle assembly 334 back to the patient 302, a small amount of blood is still typically contained in the venous access line 118 and venous needle assembly 334. In addition, as the arterial access line 116 and arterial needle assembly 326 were disconnected from the blood circuit 300 prior to reinfusion, the arterial access line 116 and arterial needle assembly 326 still typically contain blood. In order to flush and care for the patient's arterial access 346 and venous access 348, an additional flushing process using syringes 160, 162 is performed.

The access line flushing process will now be described with reference to FIGS. 2 and 3. With the arterial access line 116 clamped via clamp 338*a*, one of the syringes 160 is removed from the warming chamber 170 and attached to the end of the arterial access line 116. As previously discussed, the heating element 178 of the warming chamber 170 is turned on before beginning the hemodialysis treatment. As a result, the saline contained within the syringes 160, 162 in the warming chamber 170 is at a temperature ranging between about 30 degrees Celsius to about 38 degrees Celsius (e.g., 36.5 degrees Celsius to 37.5 degrees Celsius) by the end of the hemodialysis treatment.

Once the syringe 160 containing the warm saline is attached to the arterial access line 116, the plunger of the syringe 160 is depressed to flow the warm saline contained in the syringe 162 through the arterial access line 116, through the arterial needle assembly 326, and into the arterial access 346 of the patient 302. The warm saline provided by the syringe 160 flushes any remaining blood in the arterial access line 116, arterial needle assembly 326, and arterial access 346 (e.g., arterial port) back to the patient 302, which reduces the risk of clotting or infection at the arterial access 346. After flushing the arterial access line 116, the arterial needle assembly 326 can be disconnected from the patient 302.

With the venous access line 118 clamped using clamp 338*e*, the remaining syringe 162 is removed from the warming chamber 170 and attached to the end of the venous access line 118. As previously discussed, the saline contained within the syringe 162 is heated throughout the hemodialysis treatment by the heating element 178 to a temperature ranging between about 30 degrees Celsius to about 38 degrees Celsius (e.g., 36.5 degrees Celsius to 37.5 degrees Celsius).

Once the syringe 162 containing the warm saline is attached to the venous access line 118, the plunger of the syringe 162 is depressed to flow the warm saline contained in the syringe 162 through the venous access line 118, through the venous needle assembly 334, and into the venous access 348 of the patient 302. The warm saline provided by the syringe 162 flushes any remaining blood in the venous access line 118, venous needle assembly 334, and venous access 348 (e.g., venous port) back to the patient 302, which prevents clotting or infection at the venous access 348. After flushing the venous access line 118, the venous needle assembly 334 can be disconnected from the patient 302.

While certain embodiments have been described above, other embodiments are possible.

For example, while the heating element 178 of the warming chamber 170 illustrated in FIGS. 1 and 2 has been described as being coupled to the interior of the door 174 of the warming chamber 170, alternatively, the heating element 178 may be positioned at the bottom of the warming chamber 170 such that the heating element 178 is below the syringes 160, 162 positioned in the warming chamber 170 via clips 180, 182, 184, 186. In some implementations, the heating element 178 is positioned on a wall of the housing 172 of the warming chamber 170. For example, in some implementations, the heating element 178 is coupled to a rear wall of the housing 172 of the warming chamber 170 such that the heating element 178 is behind the syringes 160, 162 positioned in the warming chamber 170 via clips 180, 182, 184, 186. For example, the heating element 178 can be positioned on the rear wall of the housing 172 of the warming chamber 170 between clips 182 and 184.

Further, while the method for warming the fluid in the syringes has been described as automatically turning on the heating element 178 in response to closing the door 174 of the warming chamber before starting hemodialysis treatment, alternatively, the heating element 178 may be turned at other times during the treatment and reinfusion process, such as after completing hemodialysis treatment and at the start of reinfusion process. In addition, in some examples, an operator of the dialysis machine turns on the heating element 178 of the warming chamber 170 using a control provided on the touchscreen 151 of the hemodialysis machine.

While the temperature of the fluid used to flush the access lines 116, 118 has been described as being 30 degrees Celsius or more, it should be understood that the fluid could be warmed to lesser temperatures. Any temperature greater than room temperature can, for example, have a positive impact on the comfort of the patient.

In addition, while the dialysate circuit 400 has been described as including two dialysate filters 474, 480, in some examples, the dialysate circuit may only include a single dialysate filter.

While the warming chamber 170 has been described as including clips 180, 182, 184, 186 to position and retain the syringes 160, 162 in the warming chamber 170, other mechanical attachment devices, such as clamps, ties, straps, hooks, latches, etc., can alternatively or additionally be used to couple the syringes 160, 162 to the warming chamber 170. For example, in some implementations, rubber elements are used to couple the syringes 160, 162 to the warming chamber 170.

While the temperature sensors 188, 190 have been described as being positioned on the interior wall of the housing 172 of the warming chamber 170 proximate the syringes 160, 162 to measure the temperature of the warming chamber 170, alternatively the temperature sensors 188, 190 can be positioned to directly contact the exterior of the syringes 160, 162 in order to measure the temperature of the surface of the syringes 160, 162. An algorithm correlating the temperature of the surface of the syringes 160, 162 with the temperature of saline contained within the syringes 160, 162 can be used to determine the temperature of the saline in the syringes 160, 162.

Figure 5:
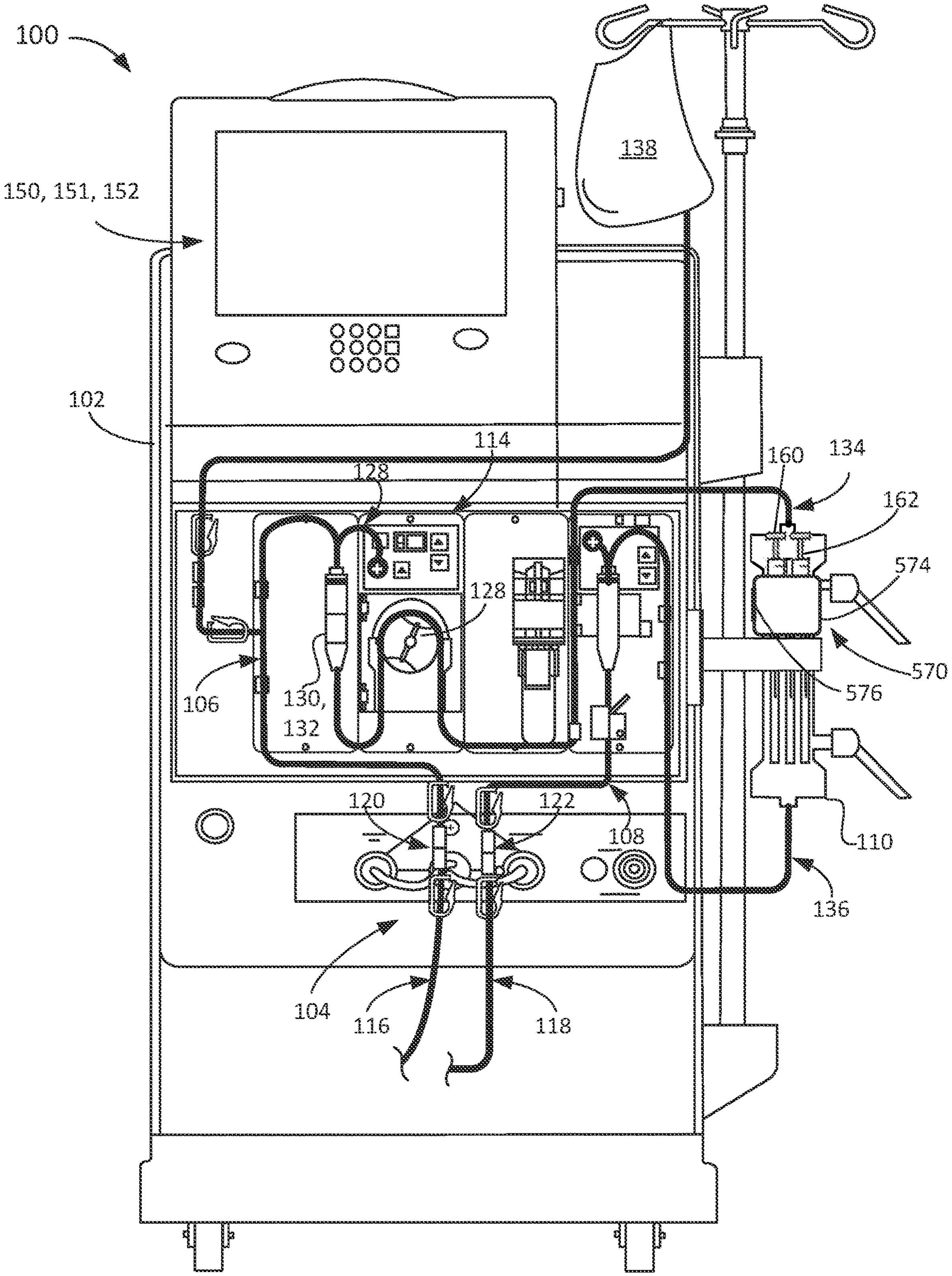
FIGS. 5-11 illustrate extracorporeal hemodialysis systems.

FIG. 5 is a schematic showing an alternate arrangement of the warming chamber of the hemodialysis machine 102. As shown in FIG. 5, the warming chamber 570 includes a door 574 that can be opened to provide access to saline-filled syringes 160, 162 positioned in the warming chamber 570. The door 574 is coupled to the dialyzer 110 of the hemodialysis machine 102 with a hinge 576. Door 574 includes an insulating material, such as plastic, fiberglass, aerogel, cellulose, or polyurethane. For example, the interior surface of the door 574 can include an insulating material to help retain heat within the warming chamber when the door 574 is in a closed position (as depicted in FIG. 5).

Figure 6:
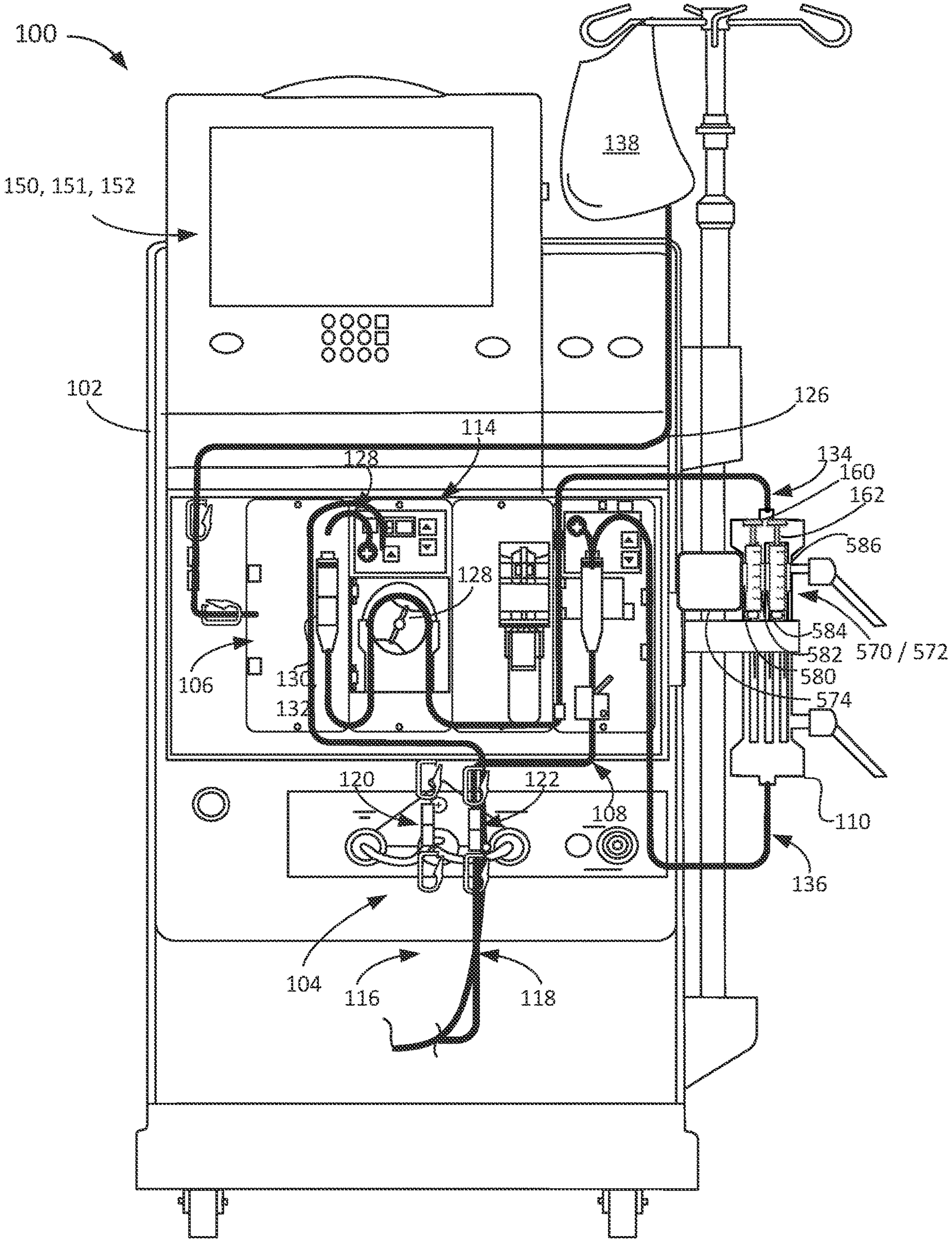

FIG. 6 depicts the door 574 of the warming chamber 570 in an open position. As depicted in FIG. 6, the warming chamber 570 includes a holder 570 with a set of clips 580, 582, 584, 586. The syringes 160, 162 are positioned adjacent to the dialyzer 110 through attachment to the clips 580, 582, 584, 586 of the holder 572. The clips 580, 582, 584, 586 of the warming chamber 570 are each coupled to the housing of the dialyzer 110 and configured to couple and position the syringes 160, 162 against the dialyzer 110. In some examples, the dialyzer machine includes a grip configured to couple and position the dialyzer 110 relative to the hemodialysis machine 102, and the grip can include receptacles for receiving the syringes 160, 162 and positioning the syringes 160, 162 adjacent the housing of the dialyzer 110. In some examples, the syringes 160, 162 may be positioned adjacent the housing 110 of the dialyzer using a strap. The strap for positioning the syringes 160, 162 adjacent the housing of the dialyzer 110 may be made of any suitable material, such as metal, fabric, or rubber, and may include any suitable fastening device, such as magnets, hook and loop fasteners, or snaps. In some examples, the straps used to position the syringes 160, 162 adjacent the housing of the dialyzer 110 can include slots for inserting the syringes 160, 162 through the strap.

As previously discussed with reference to FIG. 4, the water used to generate substitution fluid is heated by a heat exchanger of the dialysate circuit 400 prior to entering the dialyzer 110. In addition, the blood entering the dialyzer 110 from the blood circuit 300 is approximately body temperature. Thus, the fluid flowing through the dialyzer 101 is warm (about 35 degrees Celsius to about 39 degrees Celsius). The heat radiated from the fluids flowing through the dialyzer 110 is transferred to the surface of the dialyzer 110. As a result, when the syringes 160, 162 are positioned against the surface of the dialyzer 110 via clips 580, 582, 584, 586, the heat radiating from the fluid passing through the dialyzer 110 serves to warm the saline contained within the syringe 160, 162. The insulated door 574 of the warming chamber 570 covers the syringes 160, 162 and helps retain the heat transferred from the dialyzer 110 to the syringes 160, 162 within the warming chamber 570. Therefore, by positioning the syringes 160, 162 against the dialyzer 110 during hemodialysis and covering the syringes 160, 162 with the door 574 of the warming chamber 570, the saline contained in the syringes 160, 162 is heated by the heat radiated from the dialyzer 110. In some examples, the saline in the syringes 160, 162 is heated to a temperature ranging from about 30 degrees Celsius to about 38 degrees Celsius. By utilizing the heat radiated from the dialyzer 110 during hemodialysis, the warming chamber 570 warms the saline in the syringes 160, 162 without requiring an extra heat source, and, thus, uses less energy to heat the saline used for flushing the access lines 116, 118.

While the door 574 of the warming chamber 570 is depicted as being coupled to the dialyzer 110 via a hinge 576, other arrangements are possible. For example, the door 574 can be coupled to the dialyzer 100 using a pair of clips attached to the dialyzer 110 configured to couple to the sides of the door 574. In some implementations, the door 574 can be positioned over the syringes 160, 162 and a strap can be used to wrap around the door 574 and dialyzer 110 to hold the door 574 against the syringes 160, 162. In some implementations, the warming chamber 570 is provided as a thermal pod with a flap that may be opened to access syringes 160, 162 contained in the thermal pod and closed to retain heat within the thermal pod.

Figure 7:
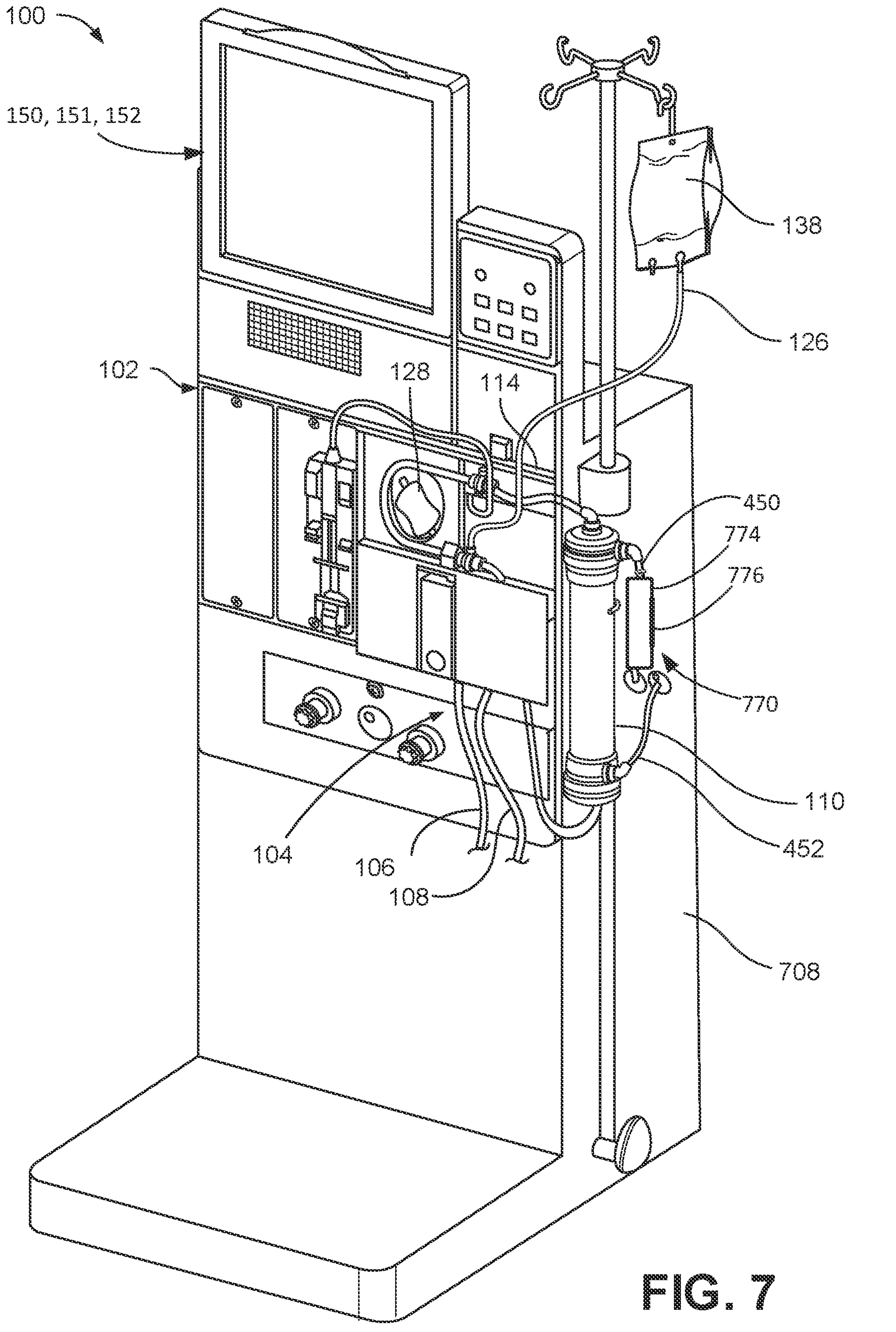

FIG. 7 is a schematic showing an alternate arrangement of the warming chamber of the hemodialysis machine 102. As shown in FIG. 7, the warming chamber 770 includes a door 774 that can be opened to provide access to saline-filled syringes 160, 162 positioned in the warming chamber 770. The door 774 is coupled to the side of the hemodialysis machine 102 via hinge 776. As depicted in FIG. 7, a portion of the dialysate inlet line 450 of the dialysate circuit 400 is positioned along a side 708 of the hemodialysis machine 102. The door 774 of the warming chamber 770 is attached to the hemodialysis machine 102 such that the door 774 is positionable to cover a portion of the dialysate inlet line 450.

Door 774 includes an insulating material, such as plastic, fiberglass, aerogel, cellulose, polyurethane, or fabric with infrared reflecting surface (e.g., aluminum foil). For example, the interior surface of the door 774 can be covered with an insulating material to help retain heat within the warming chamber 770 when the door 774 is in a closed position (as depicted in FIG. 7).

Figure 8:
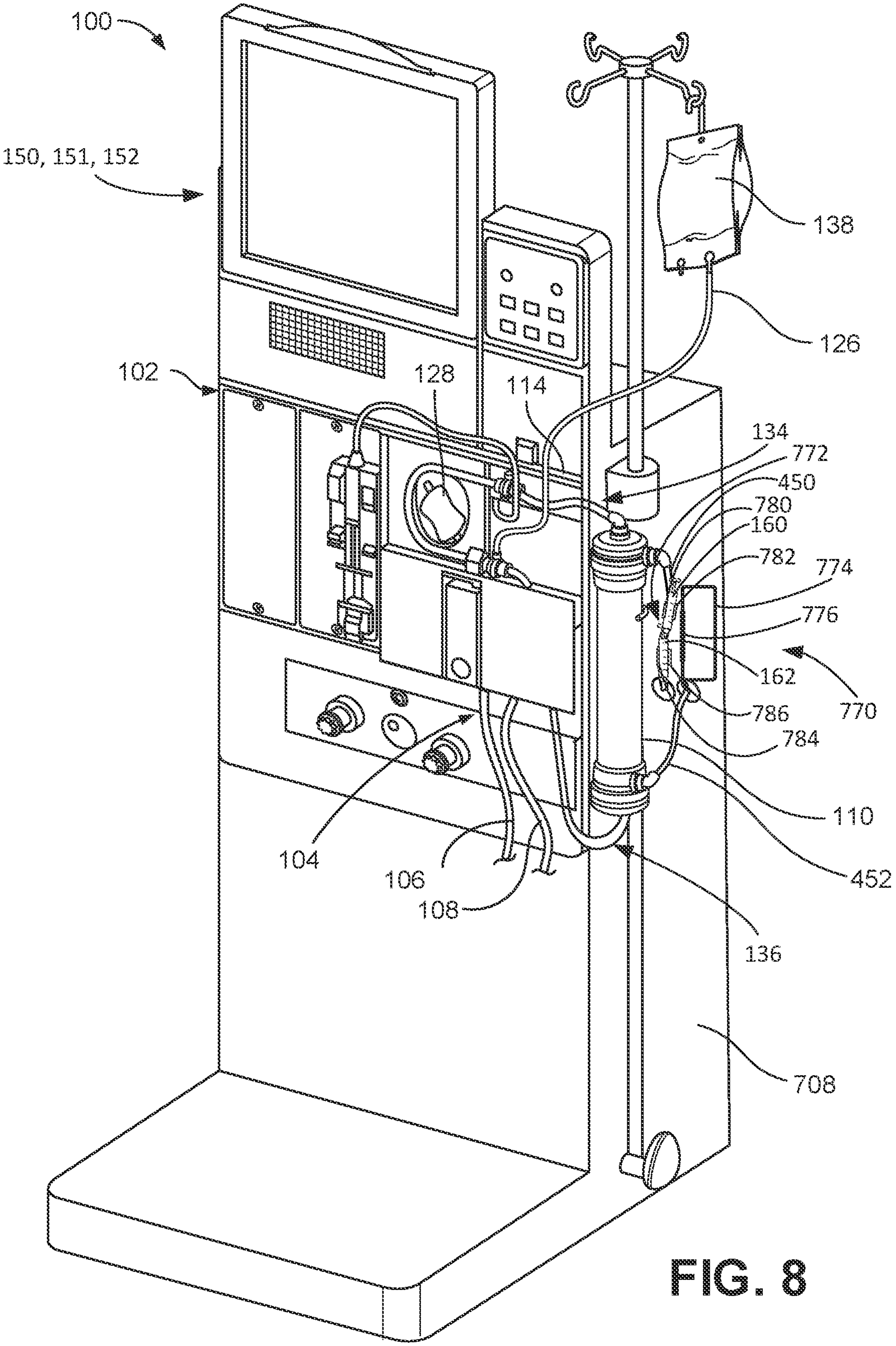

FIG. 8 depicts the warming chamber 770 with the door 774 of the warming chamber 770 in an open position. As depicted in FIG. 8, the warming chamber 770 includes holder 772 a set of clips 780, 782, 784, 786, and the syringes 160, 162 are positioned against the dialysate inlet line 450 through attachment to the clips 780, 782, 784, 786. The clips 780, 782, 784, 786 of the warming chamber 770 are each coupled to the dialysate inlet line 450 and configured to couple and position the syringes 160, 162 against the dialysate inlet line 450. In some examples, the syringes 160, 162 may be positioned adjacent the dialysate inlet line 450 using a strap. The strap for positioning the syringes 160, 162 adjacent the dialysate inlet line 450 may be made of any suitable material, such as metal, fabric, or rubber, and may include any suitable fastening device, such as magnets, hook and loop fasteners, or snaps. In some examples, the straps used to position the syringes 160, 162 against the dialysate inlet line 450 can include slots for inserting the syringes 160, 162 through the strap.

As previously discussed with reference to FIG. 4, water used the generate substitution fluid is heated by a heat exchanger of the dialysate circuit 400 prior to entering the dialyzer 110 through the dialysate inlet line 450. Thus, the substitution fluid flowing through the dialysate inlet line 450 is warm (about 35 degrees Celsius to about 39 degrees Celsius). The heat from the substitution fluid flowing through the dialysate inlet line 450 is transferred to the surface of the dialysate inlet line 450. As a result, when the syringes 160, 162 are positioned against the dialysate inlet line 450 via clips 780, 782, 784, 786, the heat radiating from the substitution fluid passing through the dialysate inlet line 450 serves to warm the saline contained within the syringe 160, 162. The insulated door 774 of the warming chamber 770 helps retain the heat transferred from the dialysate inlet line 450 to the syringes 160, 162 in the warming chamber 770. As a result, by positioning the syringes 160, 162 against the dialysate inlet line 450 during hemodialysis and covering the syringes 160, 162 with the door 774 of the warming chamber 770, the saline contained in the syringes 160, 162 is heated by the heat radiated from the dialysate inlet line 450. In some examples, the saline in the syringes 160, 162 is heated to a temperature ranging from about 30 degrees Celsius to about 38 degrees Celsius. By utilizing the heat radiated from the dialysate inlet line 450 during hemodialysis, the warming chamber 770 warms the saline in the syringes 160, 162 without requiring an extra heat source, and, thus, uses less energy to heat the saline used for flushing the access lines 116, 118.

While the door 774 of the warming chamber 770 is depicted as being coupled to the side of the hemodialysis machine 102 via a hinge 776, other arrangements are possible. For example, the door 774 can be coupled to the hemodialysis machine 102 using a pair of clips attached to the side of the hemodialysis machine 102 proximate the dialysate inlet line 450, with the clips being configured to couple to the sides of the door 774. In some implementations, the door 774 can be positioned along dialysate inlet line 450 and a strap can be used to wrap around the door 774 and dialysate inlet line 450 to hold the door 774 against the syringes 160, 162.

Further, while the warming chamber 770 is depicted as being coupled to the dialysate inlet line 450, in some implementations, the warming chamber 770 is coupled to the dialysate outlet line 452. As depicted in FIG. 7, a portion of the dialysate outlet line 452 is positioned along a side 708 of the hemodialysis machine. In some examples, the clips 780, 782, 784, 786 of the warming chamber 770 can be coupled to the dialysate outlet line 452 and configured to couple and position the syringes 160, 162 against the dialysate outlet line 452. Further, the door 774 of the warming chamber 770 can be attached to the hemodialysis machine 102 such that the door 774 is positionable to cover a portion of the dialysate outlet line 452. As with the dialysate inlet line 450, the substitution fluid flowing through the dialysate outlet line 452 has heated by a heat exchanger of the dialysate circuit 400. Therefore, by utilizing the heat radiated from the dialysate outlet line 452 during hemodialysis, the warming chamber 770 positioned along the dialyzer outlet line 452 warms the saline in the syringes 160, 162 without requiring an extra heat source, and, thus, uses less energy to heat the saline used for flushing the access lines 116, 118.

While the syringes 160, 162 have been described as being pre-filled with saline prior to placement in the warming chamber 170 of the hemodialysis machine 102, the syringes can alternatively be filled with saline after being positioned in the warming chamber.

Figure 9:
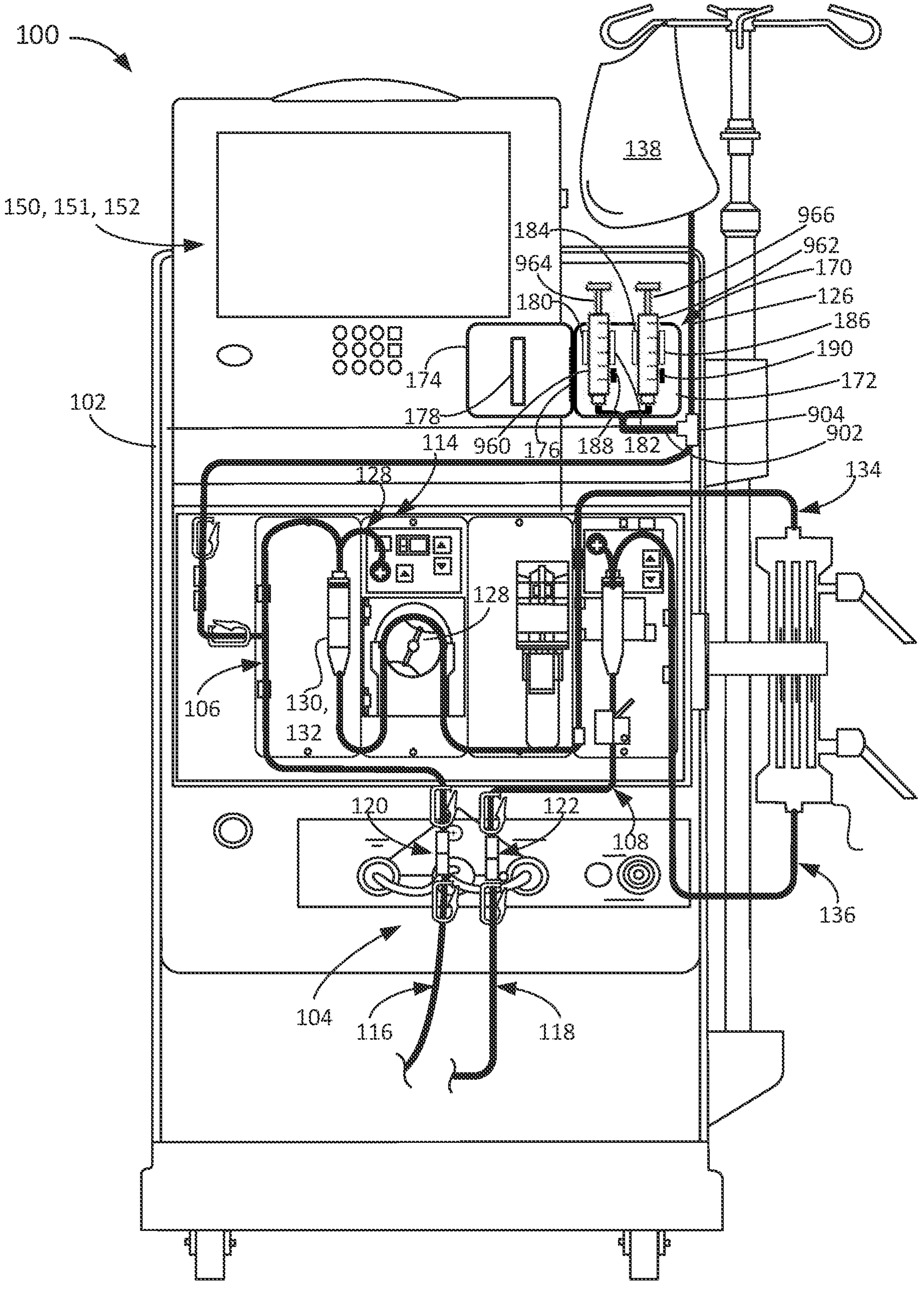

For example, FIG. 9 depicts an arrangement in which the syringes 960, 962 are fluidly coupled to the saline line 126 of the hemodialysis machine 102 for filling the syringes 960, 962 with saline. As depicted in FIG. 9, the syringes 960, 962 are positioned in the warming chamber 770 and a fluid line 902 connects each of the syringes 960, 962 to the saline line 126.

A method of filling the syringes 970, 972 with saline from the saline line 126 will now be described with reference to FIG. 9. After priming the hemodialysis machine 102, the syringes 960, 962 are positioned within the warming chamber 170 using clips 180, 182, 184, 186, and an end of each syringe is coupled to the fluid line 902. A connector 904 is attached to an end of the fluid line 902 to fluidly couple the fluid line 902 to the saline line 126 of the hemodialysis machine 102. Once the syringes 960, 962 are positioned within the warming chamber 170 and fluidly coupled to the saline line 126 via fluid line 902, the motor of the blood pump 128 of the hemodialysis machine is run in reverse, causing increased pressure in the saline line 126 and thus filling the syringes 960, 962 with saline from the saline line 126. Once the syringes 960, 962 have been filled with saline from the saline line 126, the heating element 178 can be turned on to warm the saline in the syringes 960, 962, and the hemodialysis treatment and reinfusion can proceed as described above.

Figure 10:
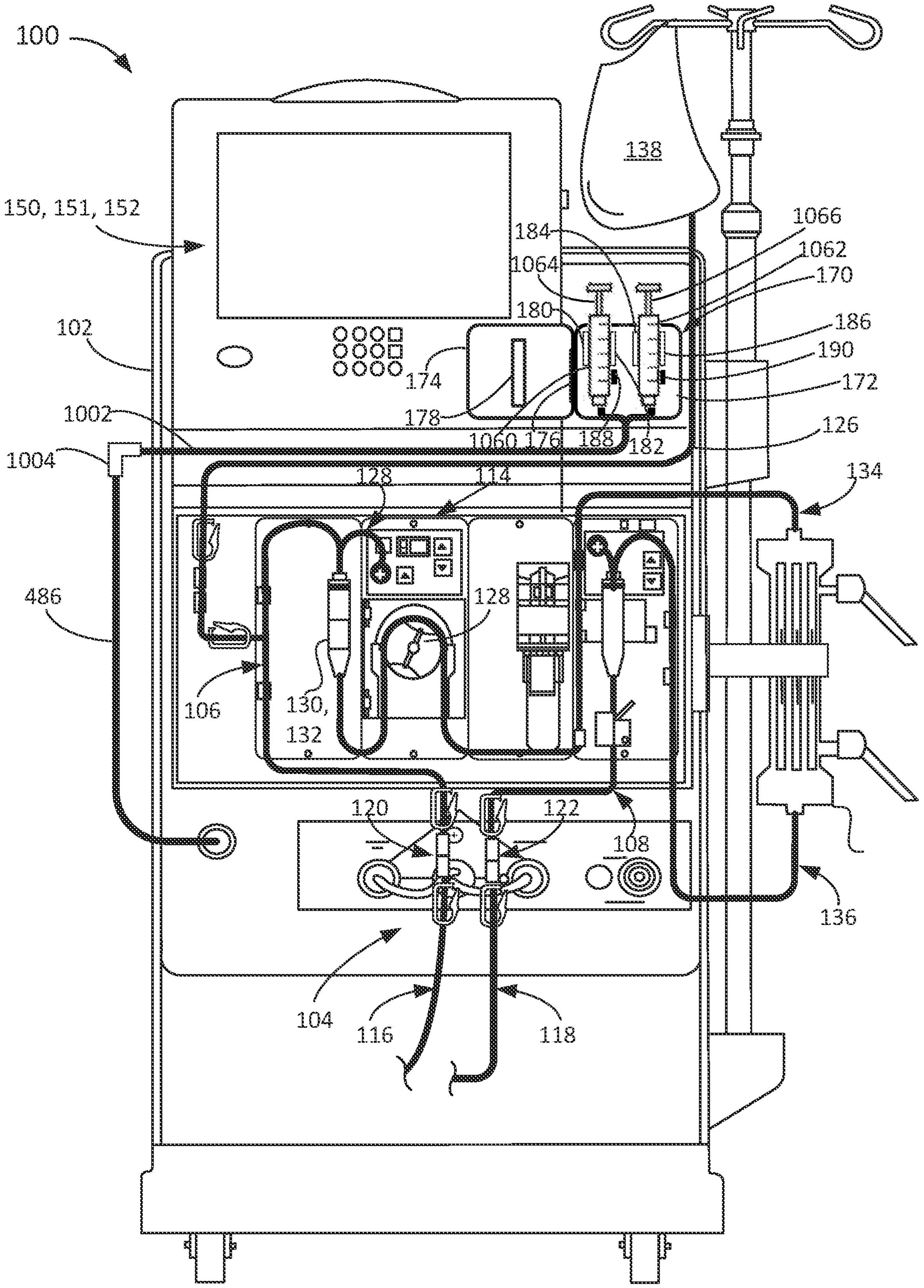

FIG. 10 depicts an arrangement in which syringes 1060, 1062 are fluidly coupled to the substitution line 486 of the hemodialysis machine 102 for filling the syringes 1060, 1062 with saline. As depicted in FIG. 9, the syringes 1060, 1062 are positioned in the warming chamber 770 and a fluid line 1002 connects each of the syringes 960, 962 to the substitution fluid line 486.

A method of filling the syringes 1060, 1062 with saline from the substitution fluid line 485 will now be described with reference to FIGS. 4 and 10. After priming the hemodialysis machine 102, the syringes 1060, 1062 are positioned within the warming chamber 170 using clips 180, 182, 184, 186 and an end of each syringe is coupled to the fluid line 1002. A connector 1004 is attached to an end of the fluid line

1002 to fluidly couple the fluid line 1002 to the substitution fluid line 486 of the hemodialysis machine 102. Once the syringes 1060, 1062 are positioned within the warming chamber 170 and fluidly coupled to the substitution fluid line 486 via fluid line 1002, the substitution pump 488 of the hemodialysis machine 102 is run to draw substitution fluid generated by the dialysate circuit 400 through the substitution fluid line 486 and the fluid line 1002, causing increased pressure in the substitution fluid line 486 and thus filling the syringes 1060, 1062 with substitution fluid. In some examples, the plungers of the syringes 1060, 1062 can be withdrawn manually by an operator of the hemodialysis machine 102 to fill the syringes 1060, 1062 with substitution fluid from the substitution fluid line 486. Once the syringes 1060, 1062 have been filled with substitution fluid from the substitution fluid line 486, the substitution pump 488 is turned off and the heating element 178 is turned on to warm the substitution fluid contained in the syringes 1060, 1062, and hemodialysis treatment and reinfusion can proceed as described above.

Further, while FIG. 10 depicts the syringe 1060, 1062 being positioned in a warming chamber 170 and the fluid in the syringes 1060, 1062 being warmed by a heating element 178 of the warming chamber 170, alternatively, the syringes 1060, 1062 can be filled with warm substitution fluid directly from the hemodialysis machine 102 without requiring additional heating from a warming chamber. For example, following hemodialysis treatment, the syringes 1060, 1062 can be fluidly coupled to the substitution fluid line 486 via a fluid line 1002 and the substitution pump 486 of the dialysate circuit 400 can be run to deliver warm substitution fluid from the dialysate circuit 400 to the syringes 1060, 1062 via the substitution fluid line 486 and the fluid line 1002. As previously discussed, the water used to generate substitution fluid is warmed by a heat exchanger of the dialysate circuit 400 before being provided to the substitution fluid line 486. Therefore, the substitution fluid provided by the substitution fluid line 486 is already warm (e.g., about 34 degrees Celsius to about 39 degrees Celsius). Since the process of reinfusion and flushing the access lines 116, 118 is performed immediately following hemodialysis treatment, the substitution fluid provided to the syringes 1060, 1062 via the substitution fluid line 486 following treatment would still be warm during reinfusion and flushing of the access lines. Therefore, a warming chamber to warm the fluid in the syringes 1060, 1062 is not necessary when the syringes 1060, 1062 are filled with substitution fluid directly from the substitution line 486 following hemodialysis treatment.

While the hemodialysis system 100 has been described as including a pair of syringes 160, 162 to store fluid for flushing the access lines 116, other fluid receptacles, can alternatively or additionally be used to store fluid for flushing the access lines 116, 118. In some implementations, one or more fluid-filled bags are used to store the fluid for flushing the access lines 116, 118, and the warming chamber 170 is configured to couple to the one or more bags and warm the fluid contained in the bags. In some examples, a single fluid-filled syringe is used to flush both of the access lines 116, 118. In some implementations, three or more fluid-filled syringes are used to flush the access lines 116, 118.

Figure 11:
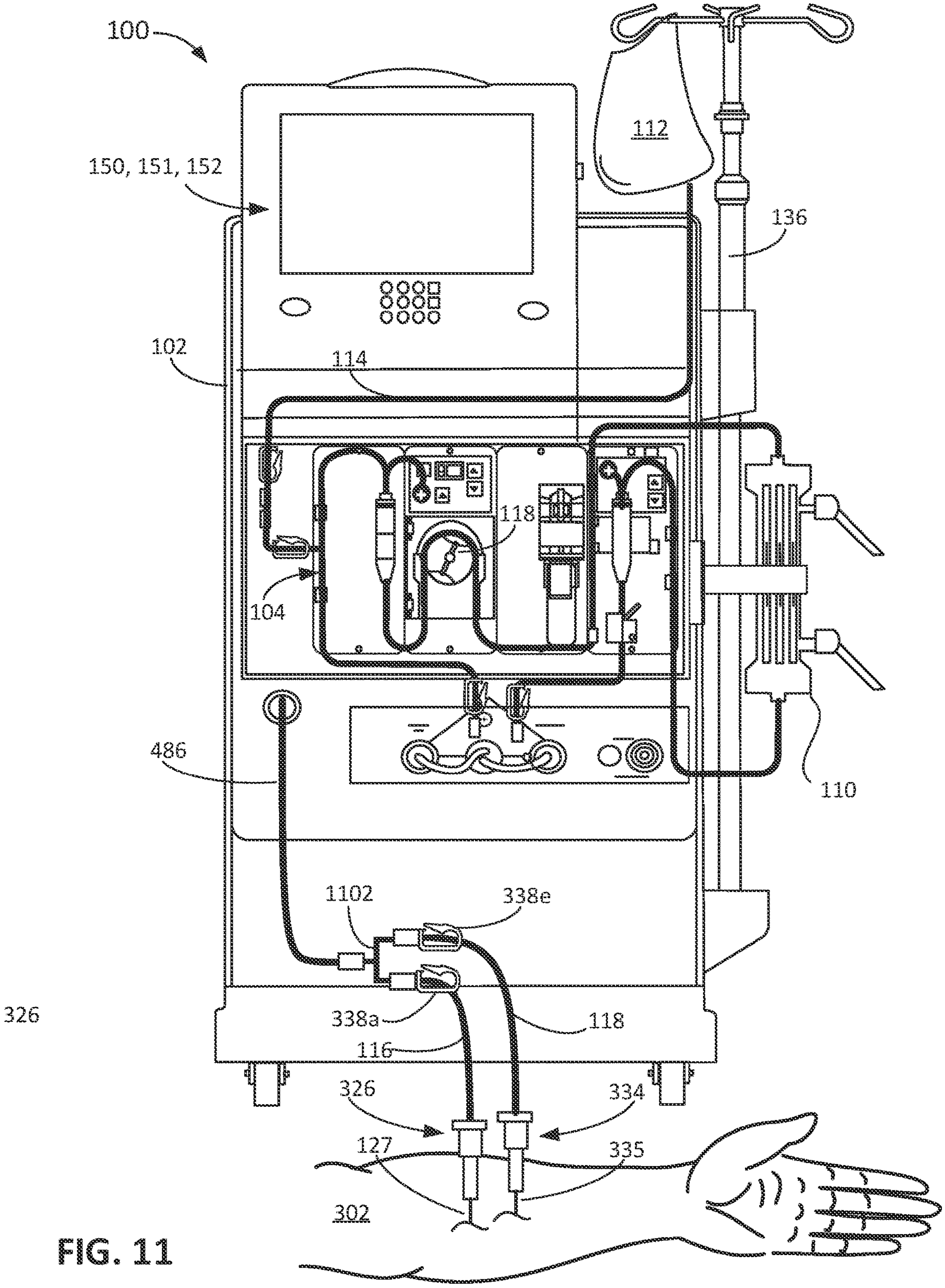

Further, in some implementations, rather than flushing the access lines 116, 118 with fluid contained in a fluid receptacle, such as a syringe, the access lines 116, 118 are connected to the substitution fluid line 486 and flushed with substitution fluid provided by the substitution fluid line 486. For example, as depicted in FIG. 11, following hemodialysis treatment and reinfusion, the arterial access line 116 and the venous access line 118 can be coupled to the substitution fluid line 486 via a connector 1102. Once the access lines 116, 118 are fluidly coupled to the substitution fluid line 486 via the connector 1102, the substitution pump 488 of the dialysate circuit 400 is run to draw warm substitution fluid from the dialysate circuit 400 through the substitution fluid line 486 and connector 1102, and into the access lines 116, 118. As previously discussed with reference to FIG. 4, the water used to generate the substitution fluid is heated by a heat exchanger of the dialysate circuit 400 prior to the substitution fluid entering the substitution fluid line 486. Therefore, the substitution fluid provided to the access lines 116, 118 via the substitution fluid line 486 is already warm (e.g., about 34 degrees Celsius to about 39 degrees Celsius).

While FIG. 11 depicts the access lines 116, 118 being connected to the substitution line simultaneously using a connector 1102, alternatively, the arterial access line 116 and the venous access line 118 can each be individually connected to the substitution fluid line 486 and flushed with substitution fluid individually. For example, following hemodialysis treatment, clamps **338*a* and 338*e* are closed to clamp the arterial access line 116 and venous access line 118, respectively, and the end of the arterial access line 116 can be fluidly coupled to the substitution fluid line 486. Once the arterial access line 116 is fluidly coupled to the substitution fluid line 486, clamp 338*a* is opened to allow flow through the arterial access line 116, and the substitution pump 488 of the dialysate circuit 400 is turned on to draw warm substitution fluid from the dialysate circuit 400 through the substitution fluid line 486 into the arterial access line 116 to flush the arterial access line 116 and arterial needle assembly 326. After flushing the arterial access line 116 and arterial needle assembly 326 of any remaining blood, the substitution pump 488 is turned off, the arterial access line 116 is detached from the substitution fluid line 486, and the arterial needle assembly 326 is removed to patient 302**.

The venous access line 118 is then fluidly coupled to the substitution fluid line 486 and clamp **338*e* is opened to allow fluid to flow through the venous access line 118. The substitution pump 488 of the dialysate circuit 400 is turned on to draw warm substitution fluid from the dialysate circuit 400 through the substitution fluid line 486 into the venous access line 118 to flush the venous access line 118 and venous needle assembly 334. After flushing the venous access line 118 and venous needle assembly 334 of any remaining blood, the substitution pump 488 is turned off, the venous access line 118 is detached from the substitution fluid line 486, and the venous needle assembly 334 is removed to patient 302**.

While the process of flushing the access line 116, 118 via direct connection of the access lines 116, 118 to the substitution fluid line 486 is described as flushing the arterial access line 116 before flushing the venous access line 118, alternatively, the venous access line 118 can be flushed prior to flushing the arterial access line 116.

A number of embodiments have been described. Nevertheless, it will be understood that various modifications may be made without departing from the spirit and scope of the disclosure. Accordingly, other embodiments are within the scope of the following claims.

What is claimed is:

1. An extracorporeal blood treatment system comprising:

a syringe configured to be filled with fluid received from a fluid line of the extracorporeal blood treatment system;

an extracorporeal blood treatment apparatus comprising a warming chamber configured to receive the syringe and to heat the fluid contained in the syringe; and a blood component set configured to be coupled to the extracorporeal blood treatment apparatus to convey fluid from a patient, through a dialyzer, and back to the patient during extracorporeal blood treatment, the blood component set comprising an access line;

wherein the syringe is configured to be coupled to the access line following the extracorporeal blood treatment to deliver the fluid from the syringe into the access line to infuse blood to the patient following the extracorporeal blood treatment.

2. The system of claim 1, wherein:

the syringe is coupled to a saline line of the blood component set; and the syringe is filled with saline from the saline line.

3. The system of claim 2, wherein:

the syringe comprises a plunger that can be actuated to draw saline from the saline line into the syringe.

4. The system of claim 1, wherein:

the syringe is coupled to a substitution line of the extracorporeal blood treatment apparatus; and the syringe is filled with substitution fluid from the substitution line.

5. The system of claim 4, wherein:

the syringe comprises a plunger that can be actuated to draw substitution fluid from the substitution line into the syringe.

6. The system of claim 1, wherein the warming chamber comprises:

a housing; and a heating element coupled to the housing and configured to heat the fluid in the syringe.

7. The system of claim 6, wherein:

the heating element is coupled to a door of the housing; and the housing is configured to position the syringe proximate the heating element when the door of the housing is in a closed position.

8. The system of claim 7, wherein the heating element is configured to automatically turn on in response to closing the door of the housing.

9. The system of claim 6, wherein:

the heating element is positioned proximate a bottom of the housing; and the housing is configured to position the syringe above the heating element.

10. The system of claim 6, wherein:

the heating element is positioned along a wall of the housing, and the housing is configured to position the syringe proximate the heating element.

11. The system of claim 6, wherein the heating element is spaced apart from the syringe when the syringe is positioned within the housing.

12. The system of claim 6, wherein the heating element comprises an infrared heater.

13. The system of claim 6, wherein the heating element comprises a photonic heater.

14. The system of claim 1, where the warming chamber comprises one or more mechanical attachment devices configured to position of the syringe within a housing of the warming chamber.

15. The system of claim 1, wherein the warming chamber comprises one or more temperature sensors configured to measure a temperature inside the warming chamber.

16. The system of claim 1, wherein the warming chamber comprises a holder configured to position the syringe adjacent a fluid line set to warm the fluid in the syringe.

17. The system of claim 16, wherein the fluid line set comprises a dialysate line configured to provide dialysate to the dialyzer of the extracorporeal blood treatment system.

18. The system of claim 16, further comprising an insulated door coupled to the holder and configured to cover the syringe coupled to the holder.

19. The system of claim 1, wherein the warming chamber comprises a holder configured to position the syringe against the dialyzer to warm fluid in the syringe.

20. The system of claim 19, further comprising an insulated door coupled to the holder and configured to cover the syringe coupled to the holder.

* * * * *